(12) United States Patent
Rothberg

(10) Patent No.: US 7,551,294 B2
(45) Date of Patent: Jun. 23, 2009

(54) SYSTEM AND METHOD FOR BREWSTER ANGLE STRADDLE INTERFEROMETRY

(75) Inventor: Lewis J. Rothberg, Pittsford, NY (US)

(73) Assignee: University of Rochester, Rochester, NY (US)

( * ) Notice: Subject to any disclaimer, the term of this patent is extended or adjusted under 35 U.S.C. 154(b) by 154 days.

(21) Appl. No.: 11/532,891

(22) Filed: Sep. 18, 2006

(65) Prior Publication Data

US 2007/0076214 A1    Apr. 5, 2007

Related U.S. Application Data

(60) Provisional application No. 60/718,248, filed on Sep. 16, 2005.

(51) Int. Cl.
G01B 11/02 (2006.01)
G01B 9/02 (2006.01)

(52) U.S. Cl. ....................... 356/504; 356/491
(58) Field of Classification Search ................ 356/491, 356/496, 364, 369, 492, 493, 503, 504
See application file for complete search history.

(56) References Cited

U.S. PATENT DOCUMENTS

| | | | |
|---|---|---|---|
| 3,612,692 A | 10/1971 | Kruppa et al. | |
| 3,985,447 A * | 10/1976 | Aspnes | 356/369 |
| 4,521,522 A * | 6/1985 | Lundstrom et al. | 436/525 |
| 4,606,638 A | 8/1986 | Sommargren | |
| 4,655,595 A * | 4/1987 | Bjork et al. | 356/369 |
| 4,857,273 A | 8/1989 | Stewart | |
| RE33,581 E | 4/1991 | Nicoli et al. | |
| 5,089,387 A | 2/1992 | Tsay et al. | |
| 5,482,830 A | 1/1996 | Bogart et al. | |
| 5,491,556 A | 2/1996 | Stewart et al. | |
| 5,494,829 A | 2/1996 | Sandstrom et al. | |
| 5,541,057 A | 7/1996 | Bogart et al. | |
| 5,550,063 A | 8/1996 | Bogart | |

(Continued)

FOREIGN PATENT DOCUMENTS

WO    91/04491 A1    4/1991

(Continued)

OTHER PUBLICATIONS

Ourmazd et al., "Si-SiO2 Transformation," Jul. 13, 1987, Phys. Rev. Letters, vol. 59, No. 2, pp. 213-216.*

(Continued)

*Primary Examiner*—Gregory J. Toatley, Jr.
*Assistant Examiner*—Scott M Richey
(74) *Attorney, Agent, or Firm*—Nixon Peabody LLP

(57) ABSTRACT

A system and method for biomolecular sensing are disclosed. The system includes a receptor for a target, a source of p-polarized light positioned to direct light toward the receptor in a manner effective to result in a condition of near perfect interference in the absence of target binding; and a detector positioned to measure any light reflected from the front and back surfaces of the coating. The receptor includes a substrate and a translucent coating on the substrate having front and back surfaces, wherein the incident angle for one of the substrate/coating interface and the medium/coating (probe) interface is greater than its Brewster angle and the incident angle for the other interface is less than its Brewster angle.

27 Claims, 19 Drawing Sheets

U.S. PATENT DOCUMENTS

| | | | |
|---|---|---|---|
| 5,552,272 A * | 9/1996 | Bogart | 435/6 |
| 5,563,707 A | 10/1996 | Prass et al. | |
| 5,629,214 A | 5/1997 | Crosby | |
| 5,631,171 A * | 5/1997 | Sandstrom et al. | 436/518 |
| 5,633,724 A | 5/1997 | King et al. | |
| 5,639,671 A | 6/1997 | Bogart et al. | |
| 5,869,272 A | 2/1999 | Bogart et al. | |
| 5,955,377 A | 9/1999 | Maul et al. | |
| 6,060,237 A | 5/2000 | Nygren et al. | |
| 6,166,818 A | 12/2000 | Nagano et al. | |
| 6,218,194 B1 | 4/2001 | Lyndin et al. | |
| 6,225,625 B1 | 5/2001 | Pirrung et al. | |
| 6,277,330 B1 * | 8/2001 | Liu et al. | 422/82.05 |
| 6,277,653 B1 | 8/2001 | Challener et al. | |
| 6,304,326 B1 * | 10/2001 | Aspnes et al. | 356/369 |
| 6,411,385 B2 * | 6/2002 | Aspnes et al. | 356/369 |
| 6,411,388 B1 | 6/2002 | Downer et al. | |
| 6,483,585 B1 | 11/2002 | Yang | |
| 6,498,335 B2 | 12/2002 | Modlin et al. | |
| 6,714,303 B2 | 3/2004 | Ivarsson | |
| 6,720,177 B2 | 4/2004 | Ghadiri et al. | |
| 6,888,639 B2 * | 5/2005 | Goebel et al. | 356/504 |
| 7,292,349 B2 * | 11/2007 | Miller et al. | 356/504 |
| RE40,225 E * | 4/2008 | Finarov | 356/630 |
| 2001/0029050 A1 | 10/2001 | Starzl et al. | |
| 2003/0112446 A1 * | 6/2003 | Miller et al. | 356/504 |
| 2003/0205681 A1 | 11/2003 | Modlin | |
| 2008/0297808 A1 * | 12/2008 | Riza et al. | 356/503 |

FOREIGN PATENT DOCUMENTS

| | | |
|---|---|---|
| WO | 02/093145 A1 | 11/2002 |
| WO | 03/036225 A1 | 5/2003 |
| WO | 03/064995 A2 | 8/2003 |
| WO | 03/065041 A1 | 8/2003 |

OTHER PUBLICATIONS

Ostroff, R., Hopkins, D. Haeberli, A.B., Baouchi, W., and Polisky, B., "Thin Film Biosensor For Rapid Visual Detection of Nucleic Acid Targets, "Clinical Chemistry 45:1659-1664 (1999).

Jenison, R., Yang, S., Haeberli, A., and Polisky, B., "Interference-Based Detection of Nucleic Acid Targets On Optically Coated Silicon," Nature Biotechnology 19:62-65 (2001).

* cited by examiner

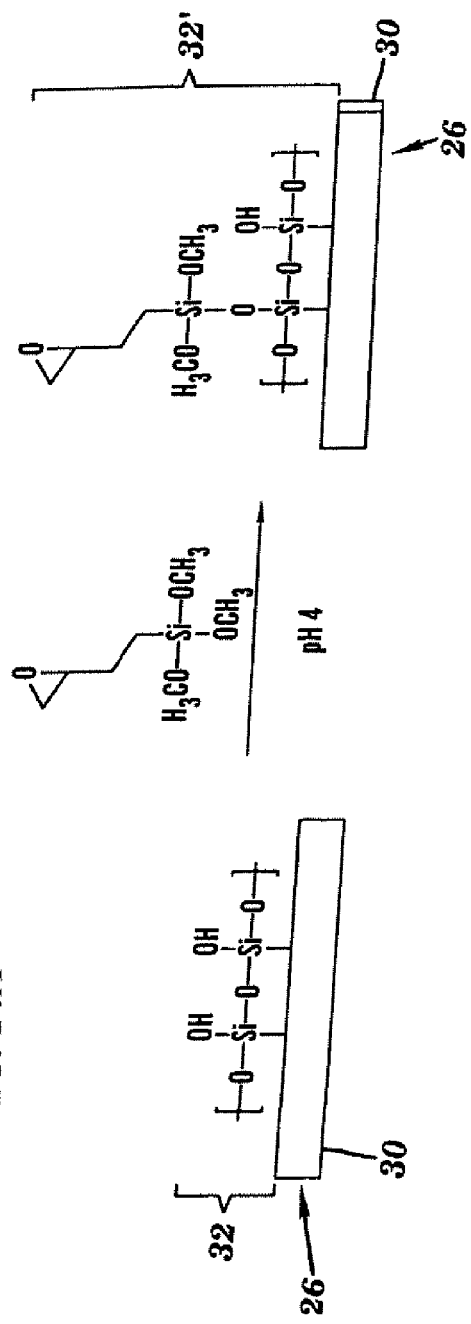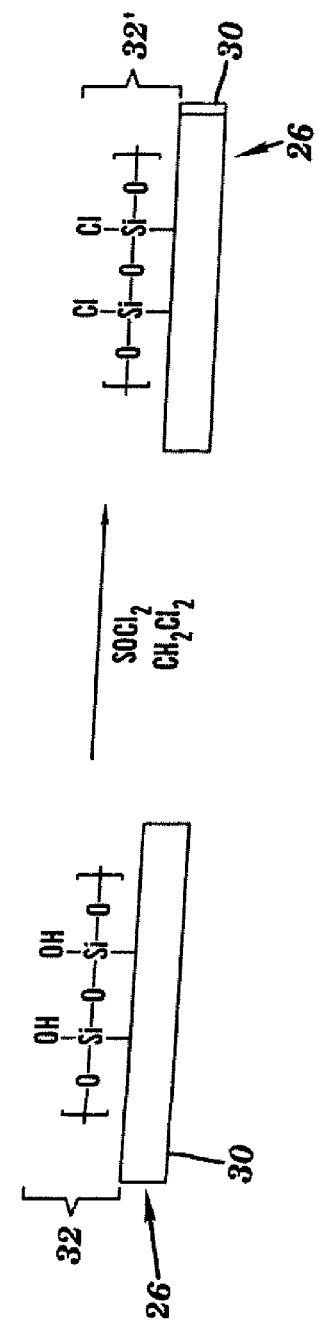
FIG. 14A
FIG. 14B

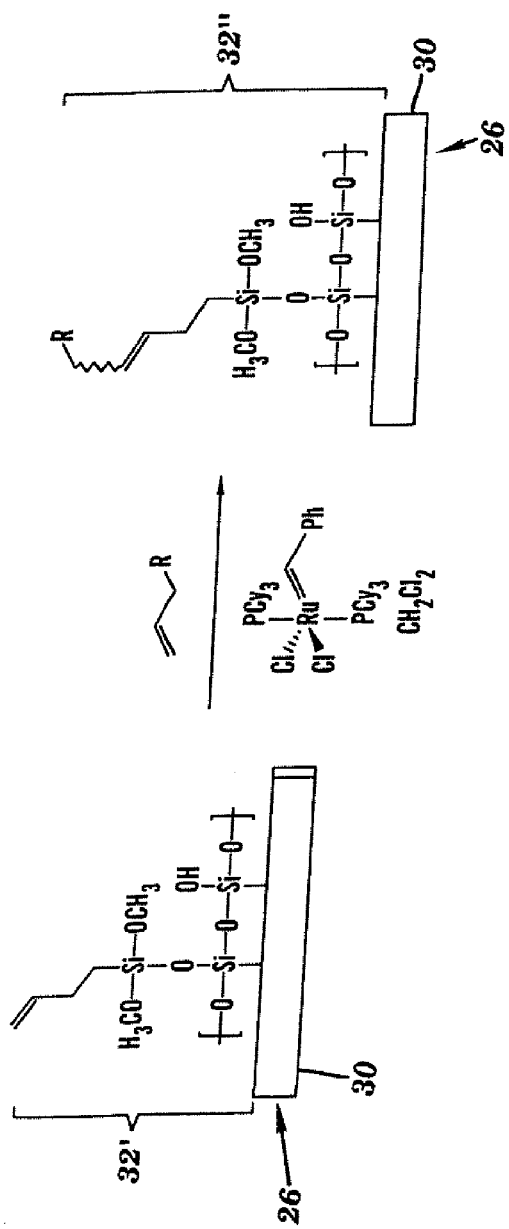
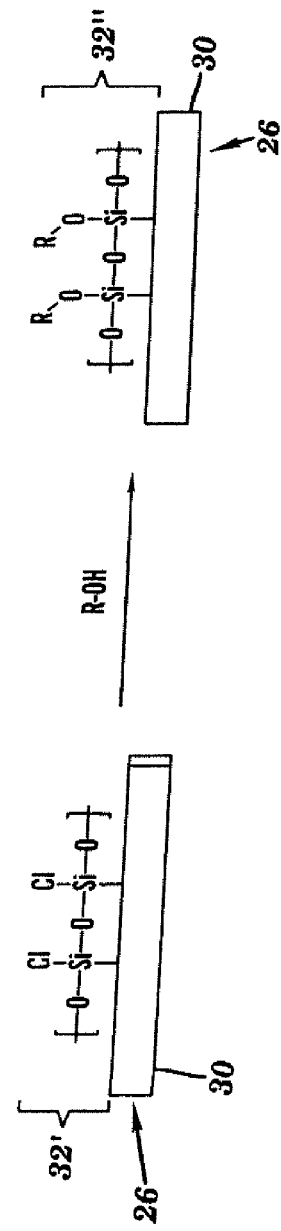
FIG. 15D
FIG. 15E

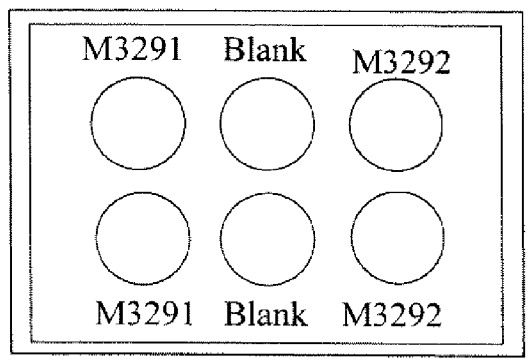
FIG. 16A
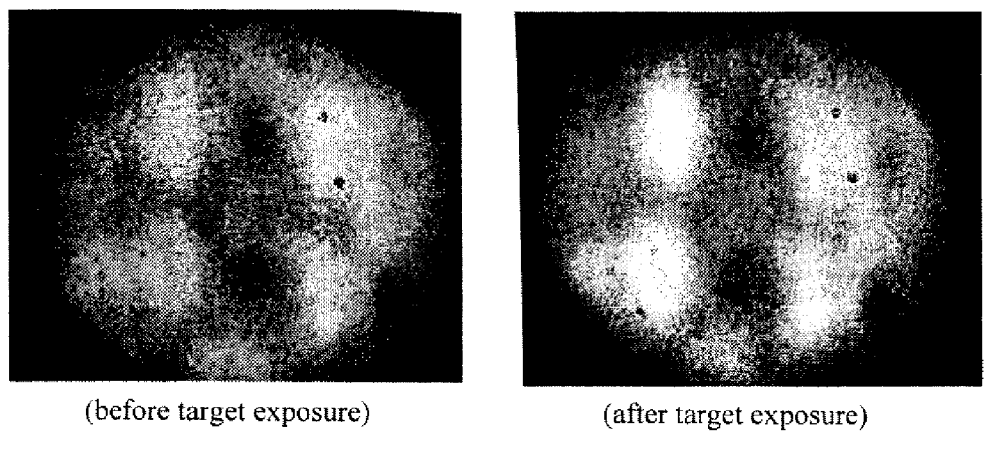
(before target exposure)     (after target exposure)
FIG. 16B
FIG. 16C
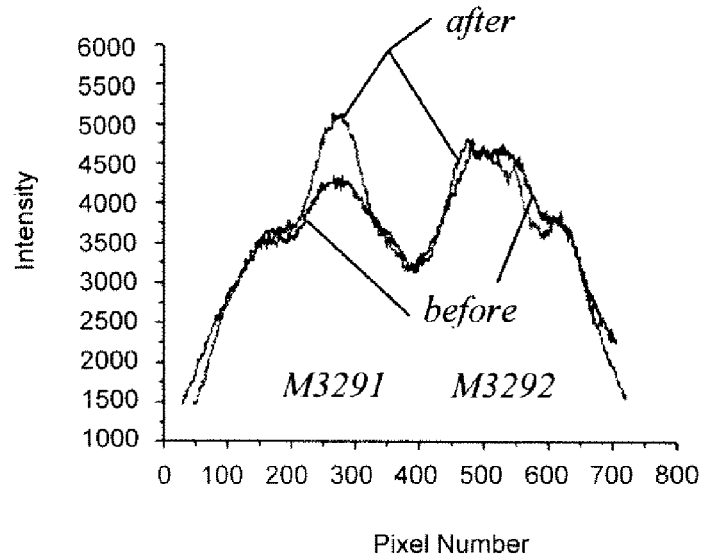

SYSTEM AND METHOD FOR BREWSTER ANGLE STRADDLE INTERFEROMETRY

This application claims the priority benefit of U.S. Provisional Patent Application Ser. No. 60/718,248, filed Sep. 16, 2005, which is hereby incorporated by reference in its entirety.

FIELD OF THE INVENTION

This invention relates to a system and method for molecular sensing or detection that utilizes Brewster angle straddle interferometry, also referred herein as p-polarized reflective interferometry ("RI").

BACKGROUND OF THE INVENTION

Microarraying and biological sensing are important emerging technologies with huge potential impact on clinical and research medicine. Present methodologies for microarraying and biological sensing are based on fluorescence, radioactive, colorimetry, or Surface Plasmon Resonance ("SPR") assays of molecular recognition chemistry. To date, the former approach has garnered the most attention.

Although these methodologies work, there are problems with each of them. Fluorescence and radioactivity require a special tagging chemistry and, thus, are time-consuming and cumbersome to use. Additionally, methodologies based on radiation are hard to scale to arrays, and have associated safety and environmental problems. Colorimetry requires chemical amplification when there are large changes in the thickness of the coating and, thus, is very complicated to adapt to arraying.

Reflective interferometry ("RI") has been demonstrated to be a powerful method for detection of adsorbate layers on surfaces. When combined with probes immobilized on a surface that are capable of selectively binding target biomolecules, RI can be used for sensitive detection of important pathogens and other applications. Experimental sensitivity to 2 Angstrom layers of adsorbates has been demonstrated and theoretical comparison with SPR predicts substantial improvements over the sensitivity of SPR if optimal geometries can be implemented. This is not surprising given the exquisite sensitivity of ellipsometric methods where the state-of-the-art is resolution in the picometer range.

The present invention is directed to overcoming these and other deficiencies in the art. The novel method of molecular sensing using Brewster angle straddle interferometry according to the present invention is capable of achieving suitably reproducible sensitivity at much lower cost using simpler equipment and less complex substrate design.

SUMMARY OF THE INVENTION

A first aspect of the present invention relates to a sensor system for sensing at least one target in a medium, the system including: a receptor for the at least one target, the receptor including a substrate and a translucent coating on the substrate having front and back surfaces; a source of p-polarized light positioned to direct at least a portion of the p-polarized light from the source toward the coating on the receptor in a manner effective to result in a condition of near perfect interference in the absence of a target bound to the receptor, wherein the incident angle for one of the substrate/coating interface and the medium/coating interface is greater than its Brewster angle and the incident angle for the other interface is less than its Brewster angle; and a detector positioned to measure the light reflected from the front and back surfaces of the coating, the detector identifying presence of at least one target based on the measured reflected light.

A second aspect of the present invention relates to a method for sensing at least one target, the method including the steps of: providing a system according to the first aspect of the present invention; directing p-polarized light at the receptor in a manner effective to achieve, in the absence of at least one target, a condition of near perfect interference between light reflected from the medium/coating interface and light reflected from the substrate/coating interface; and measuring the light reflected from the interfaces of the receptor, wherein measurement of light reflected the interfaces indicates presence of the at least one target.

A third aspect of the present invention relates to a method of quantifying the amount of a target present in a sample. This method includes repeating the measuring step according to the second aspect of the present invention both before and after exposing the receptor to a sample that contains the at least one target; and comparing the measurement of reflected light from said measurements. In addition, by comparing the difference in the two measurements, it is possible to quantify the amount of target present on the substrate based upon the degree of difference between the two measurements. This difference can be used to quantify the amount present in a sample based upon the volume of sample exposed to the receptor.

A fourth aspect of the present invention relates to a method inspecting a semiconductor wafer that includes the steps of performing the method according to the second aspect of the present invention on a semiconductor wafer, wherein said measuring is performed in one or more locations over a surface of the semiconductor wafer, and wherein the measuring of reflected light indicates the presence of debris, as the target, on the surface of the semiconductor wafer.

The present invention provides a system and method for detecting molecular adsorption based on Brewster angle straddle interferometry, which utilizes the reflectivity of p-polarized light from the medium/coating interface and the substrate/coating interface. In summary, it is possible to realize reflective interferometry with a p-polarized probe when the incidence angle on one of two interfaces is greater than its Brewster angle and the incidence angle on the other of the two interfaces is less than its Brewster angle, so that a phase flip of the reflected polarization allows nearly complete destructive interference when the coating is very thin. Measurement of films under air and water using standard polished silicon wafers with a native oxide has been performed. This has a number of salutary consequences that make this invention important for imaging of very thin (nanometer and subnanometer) films of adsorbates, as appropriate for biomolecular sensing for example. Some of these advantages include:

(1) Precise control of coating thickness is not needed since the native oxide on silicon is reproducible. Therefore, uncoated polished silicon wafers can be used. This eliminates the need to obtain coated wafers and the need to engineer them to have a very precise thickness;

(2) Relatively broadband probe light can be used without degradation of sensitivity. Thus, LEDs or filtered light are adequate. This eliminates the expense of a laser source and the imaging problems associated with optical coherence of the laser;

(3) It is possible to obtain quantitative results for film thickness using p-polarized RI by using the reflection from the very consistent bare native oxide as a reference; and (4) The angular tolerance is greater than for s-polarized reflective interferometry. This means that greater source divergence can be tolerated without degradation of sensitivity.

Another advantage of this reflective technique is that it works without any special tagging chemistry as is required for fluorescence or radioactivity. Further, the present invention can be easily adapted to arraying on a large scale and can be done in situ under standard aqueous biological media. The present invention also scales favorably with the size of adsorbate so that it should be extraordinarily sensitive to targets such as proteins, antibodies, and viruses that have been selectively bound using appropriate probes or adsorbates.

BRIEF DESCRIPTION OF THE DRAWINGS

FIG. 12B shows the chemical composition of the wafer substrate of FIGS. 12A, 12C, and 12D. FIG. 12C shows the same substrate as in FIG. 12A with the substrate moved to center OTS/bare oxide interface on the center of the probe beam profile. FIG. 12D shows the same substrate as in FIG. 12A when the substrate is under water and when the substrate is positioned so that the OTS/bare oxide interface is centered on the probe beam intensity profile.

FIGS. 14A-B illustrate silanization (14A) and halide (14B) coupling agents which can be attached, e.g., to a silicon dioxide coated receptor and used to covalently bind adsorbates (for purposes of illustration, trimethoxy(3-oxiranylpropyl)silane is shown).

FIGS. 15A-E illustrate the attachment schemes for binding adsorbates R—$NH_2$, R—SH, and R—OH upon opening of the epoxide group on the coupling agent (15A-C, respectively); adsorbate R-alkenyl to the alkenyl group on the coupling agent (15D); and adsorbate R—OH upon displacement of a halide coupling agent (15E). For purposes of illustration, trimethoxy(3-oxiranylpropyl)silane is illustrated in FIGS. 15A-C.

FIGS. 16A-C illustrate the detection of R47 RNA using an aqueous system of the type illustrated in FIG. 3. FIG. 16A shows the probe array for the receptor surface. Two probes, M3291 and M3292, with known affinities were utilized. FIG. 16B illustrates the CCD output image before (left) and after (right) exposure to the target RNA. FIG. 16C graphically illustrates as a cross-section the change in intensity of the reflected light (across the chip) before and after exposure to the target. As expected, probe M3291 binds the target effectively while probe M3292 does not.

DETAILED DESCRIPTION OF THE INVENTION

Figure 1:
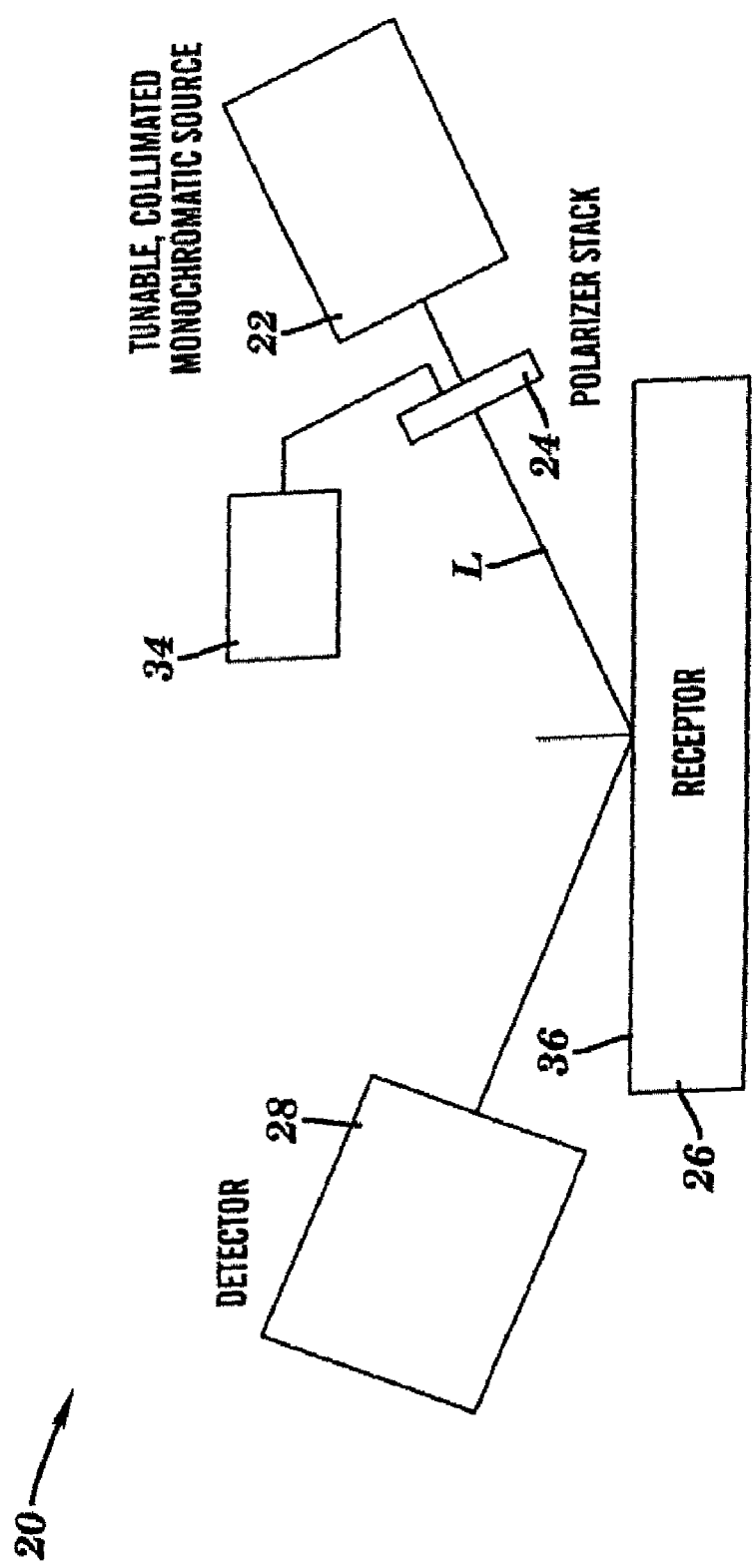
FIG. 1 is a block diagram of a biomolecular sensing system in accordance with one embodiment of the present invention.

A biomolecular sensing system 20 in accordance with one embodiment of the present invention is illustrated in FIG. 1. The sensing system 20 includes a source of p-polarized light (which as shown includes a non-polarized light source 22 and a polarizer 24), a receptor 26, and a detector 28, although the biomolecular system can have other types and arrangements of components. The present invention provides a system and method for detecting molecular adsorption based on simple reflectivity, in particular Brewster angle straddle interferometry.

Referring more specifically to FIG. 1, the light source 22 in the sensing system 20 generates and transmits a light at a set wavelength (or desired bandwidth) towards a surface of the receptor 26. In this particular embodiment the light source 22 is a collimated, monochromatic light source, although other types of light sources, such as a light source which is relatively broadband could be used. A variety of different types of light sources, such as a light-emitting diode, a laser, or a lamp with a narrow bandpass filter are ideal but even white light can also be used, though white light typically is less preferred. The medium in which the light travels from the light source 22 and polarizer 24 to the receptor 26 is air, although other types of media above the receptor, such as an aqueous environment could be used.

According to one embodiment, the polarizer 24 is positioned in the path of the light from the light source 22 and polarizes the light in a single direction, to pass substantially only p-polarized light (i.e., s-polarized light is not passed).

As an alternative to using a polarizer in addition to a non-polarized light source, a polarized light source can be utilized. A number of lasers are known to emit polarized light, such as special argon, HeNe or dye lasers.

According to another embodiment, the light incident upon the receptor can include both s- and p-polarized light, but preferably only reflected p-polarized light is detected from the reflection from the receptor. To achieve this, a polarizer can be positioned between the receptor and the detector.

According to a still further embodiment, described in greater detail below, both s- and p-polarized light can contact the receptor in a process of phase mismatch correction, which should boost sensitivity of the Brewster straddle interferometry.

Although the incident and reflected light can contain both s- and p-polarized light, from the embodiments described above it should be appreciated that the p-polarized component can be used alone as the incident light whereas the s-polarized component is never used alone.

Figure 2:
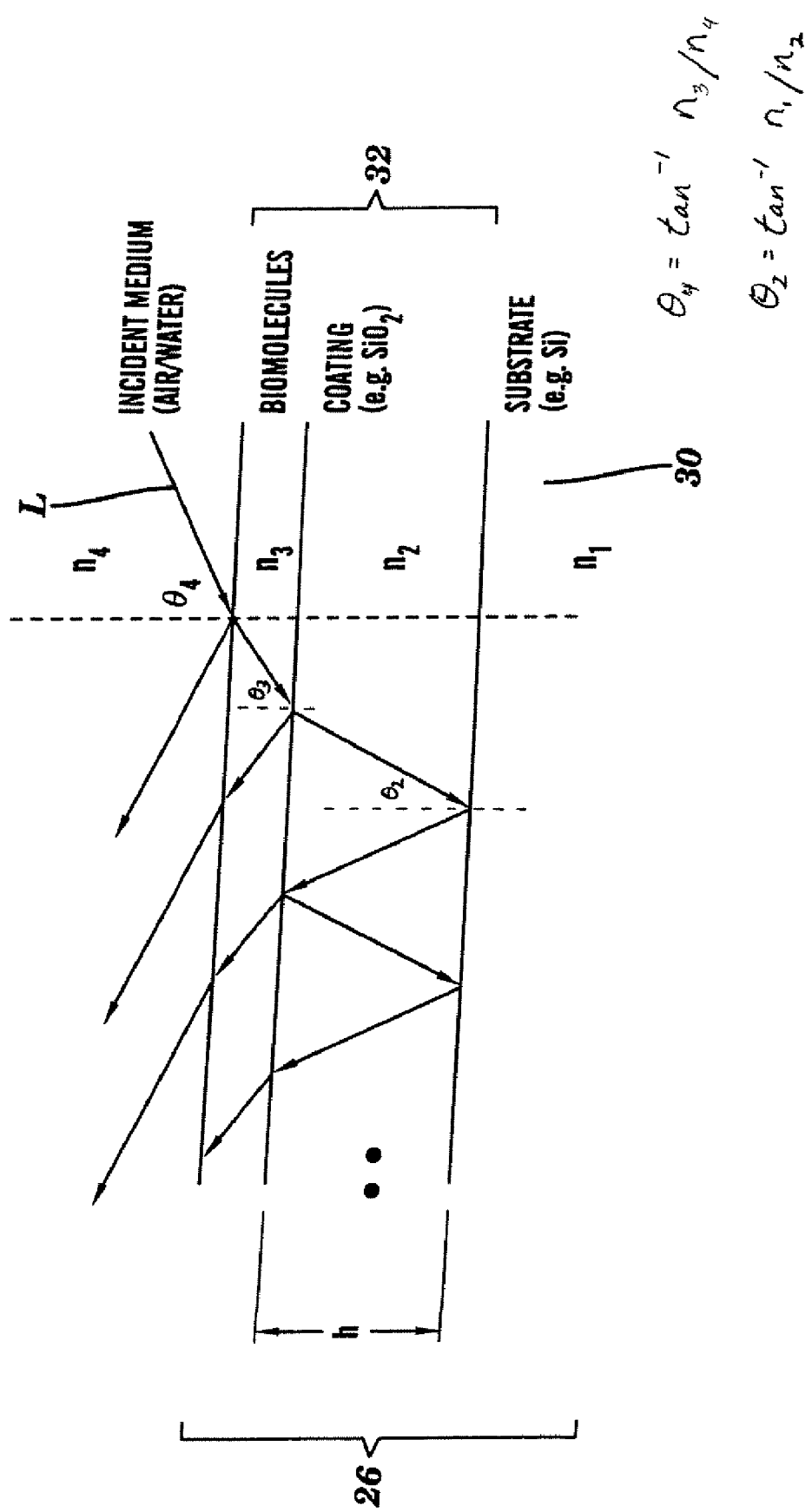
FIG. 2 is a side, cross sectional block diagram of a receptor for the biomolecular sensing system in accordance with one embodiment of the present invention.

The receptor 26 is positioned in the path of the polarized light from the polarizer 24 and includes a surface which is receptive to adsorption of one or more targets. In this particular embodiment, the receptor 26 has a substrate 30 made of silicon with a coating 32 made of silicon dioxide on one surface as shown in FIG. 2, although other types of receptors made of other materials and layers can be used. The coating 32 contains front and back surfaces, the front surface being presented to the media in which the receptor exists and the back surface being in contact with the substrate. Thus, two interfaces exist: a medium/coating interface and a coating/substrate interface.

Depending on the particular selection of coating/substrate, it is always possible to find an angle of incidence where near perfect interference can be achieved for a very thin coating when the refractive indices of the medium/coating/substrate are appropriate stepped (i.e., up or down), for example, with reference to FIG. 2, when $n_1 > n_2 > n_3 > n_4$ or when $n_4 > n_3 > n_2 > n_1$. Thus, the incident angle will be greater than the Brewster angle of one of the interfaces and less than the Brewster angle of the other interface.

As used herein, "near perfect interference" refers to the condition where the reflectivity of the coating/substrate is close to zero, preferably less than $10^{-4}$, more preferably less than $10^{-5}$, and most preferably less than $10^{-6}$. In accordance with the present invention, and distinctly different from the use of s-polarized light described in the hereinafter-referenced U.S. patent application Ser. No. 10/282,274 to Miller et al., the angle of incidence is tolerant of relatively significant deviation, up to about +1.0 degrees from incidence angle that correlates to the reflectivity minimum, while maintaining the condition of near perfect interference.

According to one embodiment, the angle of incidence for the substrate/coating interface is less than its Brewster angle and the angle of incidence for the coating/medium interface is greater than its Brewster angle. This is desired where the ratio of the substrate/coating refractive indices is greater than 1 (more preferably between about 1.2 to about 3), and the ratio of the coating/medium refractive indices is greater than 1 (more preferably between about 1.2 and about 2). An example of this embodiment includes a silicon substrate/silicon dioxide coating, and a medium that is either air or aqueous.

According to a second embodiment, the angle of incidence for the substrate/coating interface is greater than its Brewster angle and the angle of incidence for the coating/medium interface is less than its Brewster angle. This is desired where the ratio of the substrate/coating refractive indices is less than 1 (preferably between about 0.3 and about 0.9), and the ratio of the coating/medium refractive indices is less than 1 (preferably between about 0.3 and about 0.9).

It should be appreciated by those of ordinary skill in the art that any of a variety of substrates/coating can be employed in the present invention as long as their refractive indices are suitably matched to allow for angles of incidence where one but not both are above the Brewster angle for its interface.

As described in further detail hereinafter, the presence of any material on the surface of the coating, whether undesirable debris or adsorbing target molecules, effectively changes the coating thickness to afford a change in the destructive interference pattern of reflected light.

A number of suitable coatings can be employed on the substrate. Silicon dioxide (glass) is a convenient coating because it can be grown very transparent and the binding chemistries are already worked out in many cases. Other transparent glasses and glass ceramics can also be employed. In addition, the coating can be a polymer layer or silicon nitride or an evaporated molecular layer. Coating procedures for application of such coatings onto substrates are well known in the art. It should also be appreciated that certain materials inherently contain a transparent oxidized coating thereon and, therefore, such receptor surfaces inherently include a suitable coating. As noted above, a preferred substrate is silicon (e.g., a silicon wafer) because it inherently contains a substantially uniform silicon dioxide coating that is between about 1 to 3 nm (more specifically between about 2.2 to about 2.8 nm, or about 2.5 nm).

The coating itself may be capable of adsorbing a biomolecule under certain conditions. By altering the aqueous environment in which a target molecule resides, it is possible to precipitate target molecules onto the coating surfaces. Approaches for modifying the aqueous environment include, without limitation, altering pH, altering ionic strength of salt concentrations, or introducing modifiers such as non-surface bound antibodies capable of binding to and precipitating target molecules. Other known approaches can also be employed; however, such techniques are distinguishable from the use of blocking agents (e.g., bovine serum albumin or TWEEN-20) that inhibit nonspecific binding.

Alternatively, the coating of the receptor can be functionalized to include an adsorbate that is specific for a desired target molecule. In the embodiment illustrated in FIG. 2, the silicon dioxide coating on the surface of the receptor readily lends itself to modification to include thereon an adsorbate that is receptive to adsorption of the one or more targets in the sample.

As used herein, the term adsorbate refers to a compound that is attached to the coating on the receptor via a coating-binding group and also includes one or more target-binding groups. Suitable adsorbates include, without limitation, non-polymeric small molecules, polypeptides or proteins, and oligonucleotides, although other biological and non-biological adsorbates can be utilized. The coating-binding group is typically a hydroxyl or epoxy group, particularly where an oxidized coating surface is provided on the receptor. The one or more target-binding groups can include, without limitation, an amino group, a thiol, a hydroxyl, an alkyl chain, an ester, a carboxylic acid, an aromatic, a heterocycle, or a combination thereof.

Exemplary non-polymeric small molecules include, without limitation: avidin, peptido-mimetic compounds, and vancomycin. One class of peptido-mimetic compounds is disclosed in U.S. patent application Ser. No. 09/568,403 to Miller et al., filed May 10, 2000, which is hereby incorporated herein by reference in its entirety. A preferred peptido-mimetic compound which binds to lipopolysaccharide is a tetratryptophan ter-cyclopentane ("TWTCP") as disclosed in the above-noted application to Miller et al. Another class of peptidomimetic compounds that binds to the E. coli membrane protein Intimin is disclosed in U.S. Provisional Patent Application Ser. No. 60/408,403, filed Sep. 5, 2002, which is hereby incorporated herein by reference in its entirety.

Exemplary polypeptides include, without limitation, a receptor for cell surface molecule or fragment thereof, a lipid A receptor; an antibody or fragment thereof, peptide monobodies of the type disclosed in U.S. patent application Ser. No. 09/096,749 to Koide, filed Jun. 12, 1998, and U.S. patent application Ser. No. 10/006,760 to Koide, filed Nov. 19, 2001, each of which is hereby incorporated by reference in its entirety; a lipopolysaccharide-binding polypeptide; a peptidoglycan-binding polypeptide; a carbohydrate-binding polypeptide; a phosphate-binding polypeptide; a nucleic acid-binding polypeptide; and polypeptides which bind organic warfare agents such as tabun, sarin, soman, GF, VX, mustard agents, botulinium toxin, *Staphylococcus* entertoxin B, and saitotoxin.

Exemplary oligonucleotide adsorbates can be DNA, RNA, or modified (e.g., propynylated) oligonucleotides of the type disclosed in Barnes et al., *J. Am. Chem. Soc.* 123:4107-4118 (2001), and Barnes et al., *J. Am. Chem. Soc.* 123:9186-9187 (2001), each of which is hereby incorporated by reference in its entirety. The oligonucleotide adsorbates can be any length which is suitable to provide specificity for the intended target. Typically, oligonucleotide adsorbates which do not contain modified nucleotides will be at least about 12 to about 100 nucleotides in length. For oligonucleotides which contain modified bases, oligonucleotides should be at least about 7 nucleotides in length, up to about 100 nucleotides in length.

Target molecules that can be bound by the adsorbate include, without limitation: proteins (including without limitation enzymes, antibodies or fragments thereof), glycoproteins, peptidoglycans, carbohydrates, lipoproteins, a lipoteichoic acid, lipid A, phosphates, nucleic acids which are possessed or expressed by certain pathogens (e.g., bacteria, viruses, multicellular fungi, yeasts, protozoans, multicellular parasites, etc.), whole cells or particles such as viral particles, or organic compounds such as naturally occurring toxins or organic warfare agents, etc. These target molecules can be detected from any source, including food samples, water samples, homogenized tissue from organisms, air, etc.

A number of strategies are available for attaching the one or more adsorbates to the coating surface of the receptor, depending upon the type of adsorbate which is ultimately to be attached thereto.

The available strategies for attaching the one or more adsorbates include, without limitation, covalently bonding an adsorbate to the coating, ionically associating the adsorbate with the coating, adsorbing the adsorbate onto the coating, or the like. Such association can also include covalently or non-covalently attaching the adsorbate to another moiety (of a coupling agent), which in turn is covalently or non-covalently attached to the coating of the receptor.

Basically, the oxidized and hydrolyzed surface of the coating is first functionalized (i.e., primed) with a coupling agent which is attached to the surface thereof. This is achieved by providing a coupling agent precursor and then covalently or non-covalently binding the coupling agent precursor to the coating surface. The primed surface is denoted 32' in FIGS. 14A-B and FIGS. 15A-E. Once the coating surface has been primed, the adsorbate is exposed to the primed coating surface under conditions effective to (i) covalently or non-covalently bind to the coupling agent or (ii) displace the coupling agent such that the adsorbate covalently or non-covalently binds directly to the coating surface. The binding of the adsorbate to the receptor coating is carried out conditions which are effective to allow the one or more target-binding groups thereon to remain available for binding to the target molecule. The resulting functionalized coating is designated 32" in FIGS. 14A-B and FIGS. 15A-E.

Suitable coupling agent precursors include, without limitation, silanes functionalized with an epoxide group, a thiol, or an alkenyl; and halide containing compounds.

Silanes include a first moiety which binds to the coating surface and a second moiety which binds to the adsorbate. Preferred silanes include, without limitation, 3-glycidoxypropyltrialkoxysilanes with C1-6 alkoxy groups, trialkoxy (oxiranylalkyl)silanes with C2-12 alkyl groups and C1-6 alkoxy groups, 2-(1,2-epoxycyclohexyl)ethyltrialkoxysilane with C1-6 alkoxy groups, 3-butenyl trialkoxysilanes with C1-6 alkoxy groups, alkenyltrialkoxysilanes with C2-12 alkenyl groups and C1-6 alkoxy groups, tris[(1-methylethenyl) oxy]3-oxiranylalkyl silanes with C2-12 alkyl groups, [5-(3, 3-dimethyloxiranyl)-3-methyl-2-pentenyl]trialkoxysilane with C1-6 alkoxy groups, (2,3-oxiranediyldi-2,1-ethanediyl) bis-triethoxysilane, trialkoxy[2-(3-methyloxiranyl)alkyl]silane with C1-6 alkoxy groups and C2-12 alkyl groups, trimethoxy[2-[3-(17,17,17-trifluoroheptadecyl)oxiranyl]ethyl] silane, tributoxy[3-[3-(chloromethyl)oxiranyl]-2-methylpropyl]silane, and combinations thereof. Silanes can be coupled to the receptor coating according to a silanization reaction scheme shown in FIG. 14A, the conditions for which are well known to those of skill in the art. See also U.S. patent application Ser. No. 10/082,634 to Chan et al., filed Feb. 21, 2002, which is hereby incorporated herein by reference in its entirety.

Figure 15A:
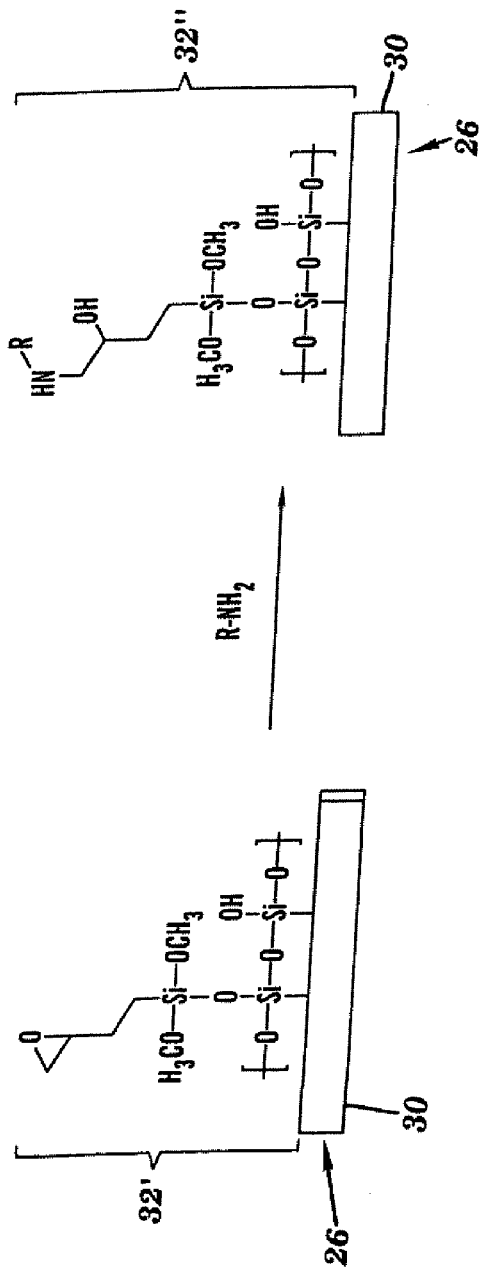
Figure 15B:
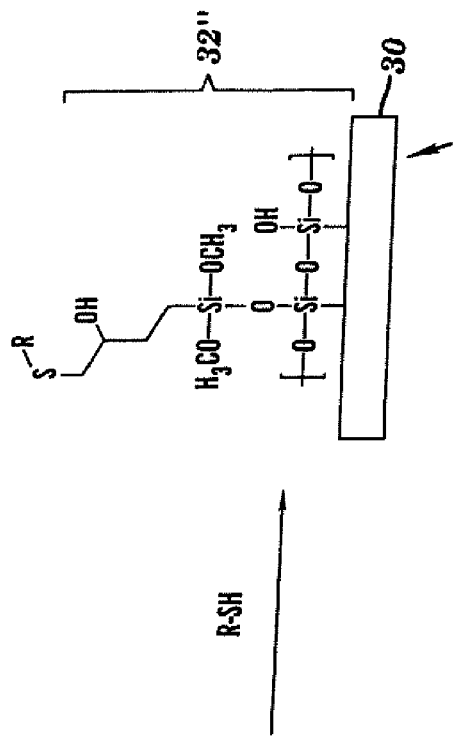
Figure 15B:
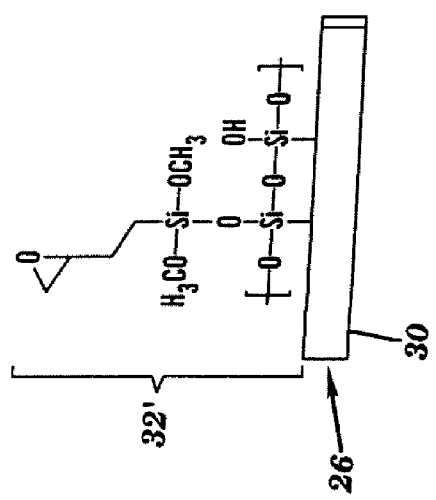
Figure 15C:
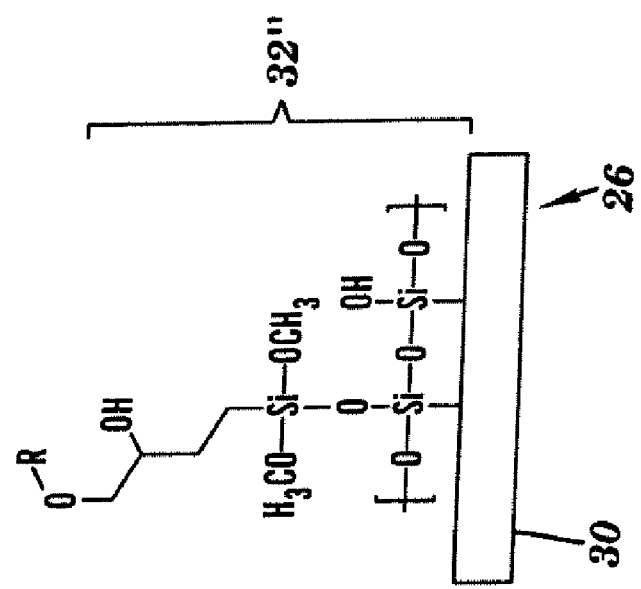
Figure 15C:
Figure 15C:
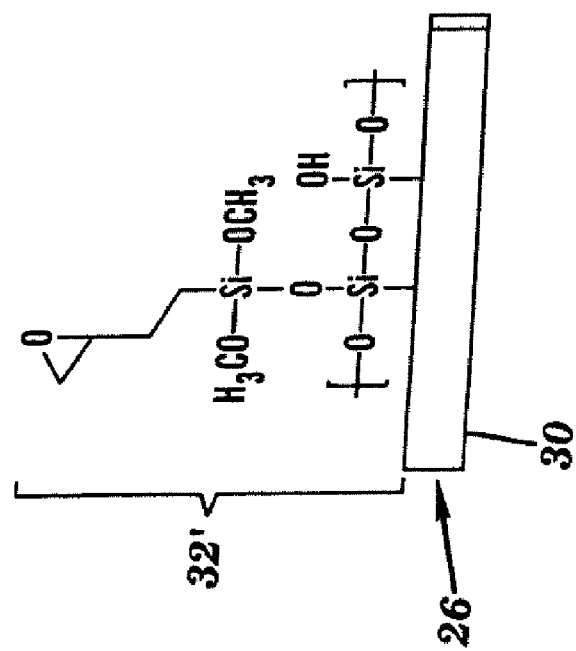

Halides can also be coupled to the receptor coating according to the reaction scheme set in FIG. 15B, the conditions for which are well known to those of skill in the art.

Thereafter, the one or more adsorbates are bound to the receptor coating according to the type of functionality provided by the coupling agent. Typically, adsorbates are attached to the coupling agent or displace the coupling agent for attachment to the receptor coating in aqueous conditions or aqueous/alcohol conditions.

Epoxide functional groups can be opened to allow binding of amino groups according to the reaction scheme set forth in FIG. 15A, the conditions for which are well known to those of skill in the art. See also U.S. patent application Ser. No. 10/082,634 to Chan et al., filed Feb. 21, 2002, which is hereby incorporated herein by reference in its entirety. Epoxide functional groups can also be opened to allow binding of thiol groups or alcohols according to the reaction scheme set forth in FIGS. 15B-C, respectively, the conditions for which are well known to those of skill in the art.

Alkenyl functional groups can be reacted to allow binding of alkenyl groups according to the reaction scheme set forth in FIG. 15D, the conditions for which are well known to those of skill in the art.

Where a halide coupling agent is employed, the halide coupling agent is typically displaced upon exposing the primed receptor coating to one or more adsorbates which contain alcohol groups as the coating-binding groups. The displacement can be carried out according to the reaction scheme set forth in FIG. 15E, the conditions for which are well known to those of skill in the art.

Where the one or more adsorbates contain two or more target-binding groups, it is possible that the target-binding groups may also interact and bind to the primed surface of the receptor coating. To preclude this from occurring to any significant extent, the primed receptor coating can also be exposed to a blocking agent. The blocking agent essentially minimizes the number of sites where the one or more adsorbates can attach to the surface of the receptor coating. Exposure to the blocking agent can be carried out prior to exposing the primed receptor coating to the adsorbates or simultaneous therewith, although simultaneous exposure is generally preferred. The blocking agents can be structurally similar to the adsorbates except that they lack a target-binding group or the blocking agents can simply be simple end-capping agents. By way of example, an amino acid alkyl ester (e.g., glycine methyl ester, glycine ethyl ester, 3-alanine methyl ester, etc.) blocking agent can be introduced to an epoxide-functionalized receptor coating as shown in FIG. 14A for attaching an adsorbate to the coupling agent, except with the amino group of glycine opening the epoxide ring and covalently binding to the coupling agent.

Referring back to FIG. 1, the detector 28 is positioned to measure the reflected light from the receptor 26. In this particular embodiment, the detector 28 measures the amplitude of the reflected light at a single polarization and ignores phase, although the detector 28 could measure for other characteristics in the reflected light. As noted above, the interference between reflected light from the front and back coating surfaces is detected and a change in the intensity pattern afforded by a particular coating results from adsorption of a target molecule or other materials (e.g., debris) to the coating surface (i.e., effectively increasing the thickness of the coating). A variety of different types of detectors can be used, such as a photodiode, photomultiplier, CCD, etc., which are desirably coupled to a standard computer (CPU with appropriate software, monitor, printer, etc.) for collecting raw data, analyzing, and presenting the same.

The reflection R from the structure shown in FIG. 1 is given by a simple analytic expression $$R=|(r_{12}+r_{23}\exp(-2i\beta))/(1+r_{12}r_{23}\exp(-2i\beta))|^2 \quad \text{Eq. (1)}$$

where $r_{jk}$ are the Fresnel reflection coefficients for TE (s-polarized) light at the interface between layer j and layer k, $n_j$ are the complex refractive indices of the various layers, $i=\sqrt{-1}$ and $\beta=(2\pi/\lambda)n_2 d \cos\theta_2$. The idea behind sensing using RI is to make the reflectivity close to zero when layer 2 is functionalized with probe molecules so that binding of target molecules disturbs that condition.

One solution for achieving near perfect interference is described in U.S. patent application Ser. No. 10/282,274 to Miller et al., filed Oct. 28, 2002, which is hereby incorporated by reference in its entirety. The implementation described therein achieves the condition that R≈0 by engineering $2\beta\approx\pi$ and $r_{12}\approx r_{23}$. The first criterion ($2\beta\approx\pi$) specifies a relationship between the wavelength, angle of incidence and layer 2 (coating) thickness, d. In particular, $d_{min}/\lambda=1/(4n_2 \cos\theta_2)$ must be satisfied. Physically, this means that light reflecting from the interface between layers 2 and 3 (coating and substrate) should travel an extra distance given by half its wavelength in medium 1. The second criterion ($r_{12}\approx r_{23}$) can be met for TE (s-polarization) where the Fresnel coefficients are given by $r_{jk}=(n_j \cos\theta_j-n_k \cos\theta_k)/(n_j \cos\theta_j+n_k \cos\theta_k)$. Physically, the second criterion makes the magnitudes of the reflections from the two interfaces equal, so that when the first criterion is satisfied, there can be near perfect destructive interference. This specifies the angle of incidence on the structure required to be $\theta_{1\ min}=\sin^{-1}(\{(n_3^2-n_2^4/n_1^2)/(n_1^2+n_3^2-2n_2^2)\}^{1/2})$. That angle is fairly large for the choices of materials in FIG. 1 because the interface between oxide and air or water is not very reflecting except far from normal incidence.

The above scheme is presumed viable and has produced results. However, a number of challenges have arisen, particularly from the single color version that would be most practical for compact and inexpensive field applications. The major challenges encountered included: (1) the need for perfect, i.e., uniform and accurate, oxide thickness, (2) coherence produces fringes that confuse pictures of microarrays, and (3) an inability to obtain quantitative data without wavelength scanning. These difficulties are described in greater detail below.

Oxide films: Criterion 1 above requires very stringent control of optical probe bandwidth so that the condition can be met exactly. The narrow bandwidth typically associated with a laser source is helpful. Criterion 2 above requires precise angle of incidence and therefore excellent collimation of the optical probe as is much more easily obtained with a laser. To use a single color laser source such as HeNe (632.8 nm), criterion 1 specifies what the coating thickness must be to achieve good destructive interference. The half-wavelength criterion leads to oxide layer thicknesses of roughly 142 nm for 632.8 nm probe radiation. Thermally grown oxides cannot be grown with such tight tolerances and, moreover, are not even perfectly uniform across a given wafer. Contrast between reflection with and without target degrades very rapidly as the oxide thickness deviates from its ideal value. An additional nuisance is that oxides that are too thin can give anomalous behavior where reflectivity decreases with target binding.

Coherence: While a laser source is desirable for the reasons noted above, the spatial and temporal coherence inherent in using a laser combined with the interferometric nature of the technique inevitably leads to fringes that complicate interpretations of reflectivity patterns associated with microarrays of molecular probe spots.

Quantitative analysis: Ideally, it would be possible to say how much target has bound for a given change in reflectivity. Because the wafer thickness is not precisely known and the collimation is imperfect, this is difficult to do in single color measurements. Calibration is not a straightforward option since each substrate has a slightly different oxide thickness. Hence, calibration bumps would be needed on every sample. Wavelength scanning gets around this problem but may have practical challenges and may prove uneconomical for a point-of-care diagnostics system. Tunable lasers may be employed but can be expensive and temperamental.

There is another approximate solution to Equation (1) for TM (p-polarization), and that solution is implemented in one embodiment of the present invention. It is readily seen that zero reflection is also achieved when $2\beta\approx 0$ and $r_{12}\approx -r_{23}$. Physically, the reason this solution is realizable is that there is a 180° phase flip in the reflected field for TM (but not TE) polarized light when the incident angle is above the Brewster angle for an interface. It turns out that it is possible to construct a system that implements a phase flip at the air (or water)/oxide interface but no phase flip at the oxide/silicon interface. For judicious choice of angle, it is therefore possible to realize $r_{12}=-r_{23}$. Thus, nearly complete destructive interference can be obtained when the waves travel nearly the same distance ($2\beta\approx 0$)—in other words, for a very thin oxide layer. Implementation of this condition with the ~2.5 nm native oxide on silicon is therefore possible and, in fact, has been successfully accomplished. Detailed solutions to the relevant equations and predicted sensitivity to target binding for this configuration are described below, but an explanation of how this variation of reflective interferometry ("RI") solves each of the problems itemized above is first presented.

First, the problem of coating thickness engineering is essentially eliminated. The thickness of the oxide is very small compared to any wavelength one can reasonably use so the condition $2\beta\approx 0$ is always achievable. In fact, modeling shows that there is little wavelength dependence to the reflectivity when used in the TM configuration. This is not surprising because the accumulated phase difference between the two interfacial reflections is very small regardless of wavelength. One consequence of this is that a well-collimated lamp with a broadband filter or a bright LED is an excellent source in this implementation of RI. Because of the finite oxide thickness, slightly less perfect interference is obtained than for the ideal TE polarized geometry ($10^{-4}$-$10^{-5}$ for TM versus $10^{-5}$-$10^{-9}$ for TE), but modeling suggests this will not turn out to be a practical limitation since suitable reflectivity is still obtainable and changes in reflectivity of factors of ~2 for 1 nm target adsorption are expected. One very welcome consequence is that any polished silicon wafer can be utilized to implement RI so that the expense, delay and imprecision associated with growing thermal oxide films can be eliminated with the preferred embodiment. Moreover, as described below, other embodiments of the invention can overcome this reduction in interference.

Second, the problem of coherence is also reduced. While the TM implementation remains an interference effect, coherence problems appear to be diminished empirically with a laser and, moreover, the lack of narrow bandwidth requirement means that even incoherent light sources can be used.

Third, the problem of being quantitative with a single color probe is also greatly simplified. The native oxide thickness is very reproducibly 2.5 nm thick and the absolute reflectivity has a straightforward relationship to the thickness of layer 2 via solution of Equation (1). Reflectivity can never decrease with target binding so there is never any ambiguity in interpreting reflectivity maps as is possible using TE with the previously identified implementation of RI. The only unknown is the angular divergence of the incident light source and this is easily measured by comparing the experimental ratio of TM to TE reflection on the bare oxide to the theoretical value since the laser bandwidth is negligible and the oxide thickness is reproducible and is known precisely.

There is even one more benefit to the p-polarized RI, which is that it turns out to be relatively insensitive to angular divergence and almost completely insensitive to source bandwidth. As described below, angular divergences of up to about a degree or more and probe bandwidths even larger than 50 nm can be utilized with substantial sensitivity. Broader probe bandwidths do not appreciably degrade the ability to measure surface topology with a few Angstroms resolution. For example, 2 nm spots can be visualized with white light (300 nm bandwidth).

Figure 4:
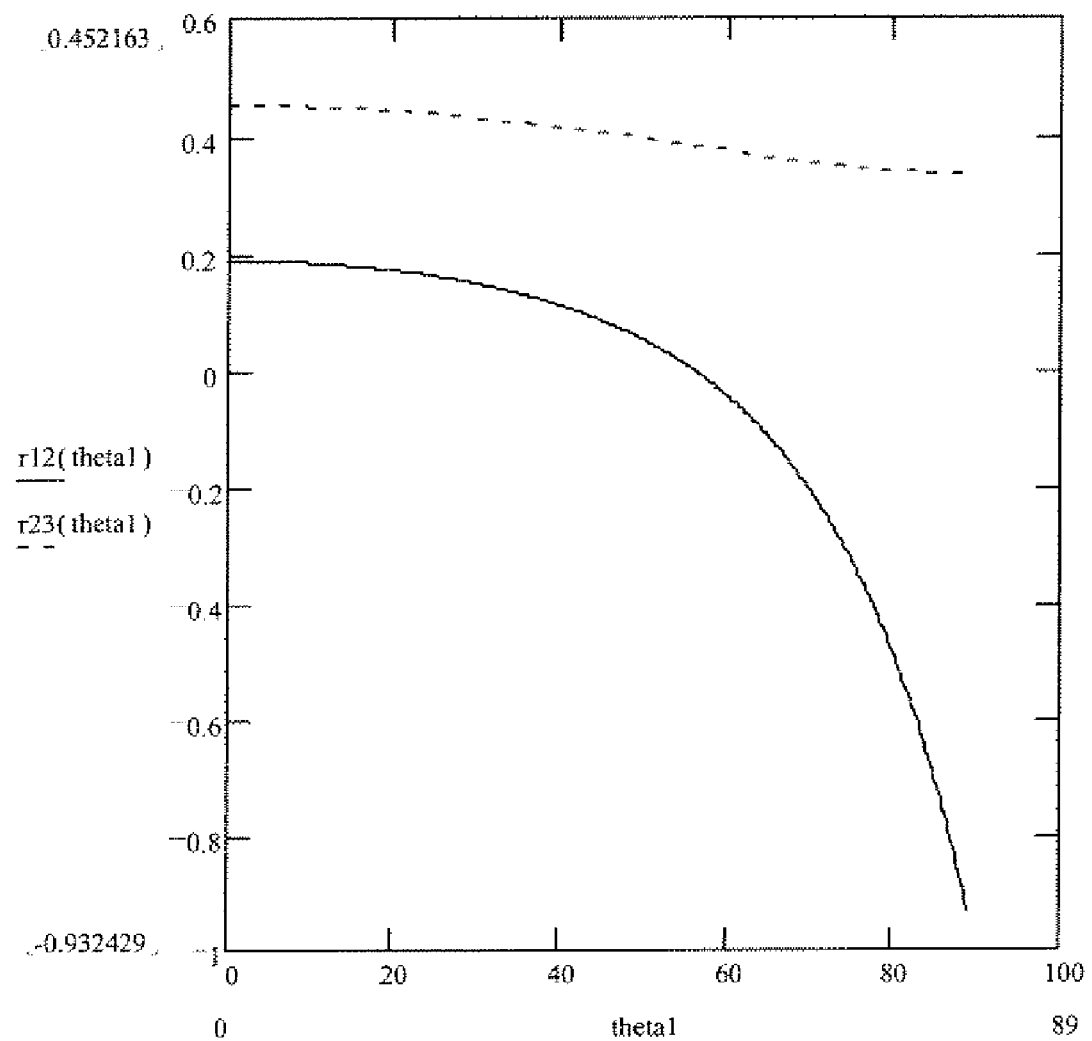
FIG. 4 is a graph showing the Fresnel coefficients for the reflected amplitude of p-polarized light at the air/$SiO_2$ ($r_{12}$) and $SiO_2$/silicon ($r_{23}$) interfaces for 632.8 nm light.

Using an approximate numerical model it is possible to numerically compute an approximate angle where $r_{12}=-r_{23}$ by plotting the Fresnel equations that define these reflection coefficients. This can be done for both the case of air above the oxide and water above the oxide. FIG. 4 plots $r_{12}$ and $r_{23}$ for the structure in FIG. 1 assuming the layer where the light is incident is air. It is clear that they become nearly equal in magnitude and opposite in sign in the neighborhood of 75.5° incidence angle. Their magnitudes are roughly 0.4 meaning that the reflection from each face is around 15%.

Figure 5:
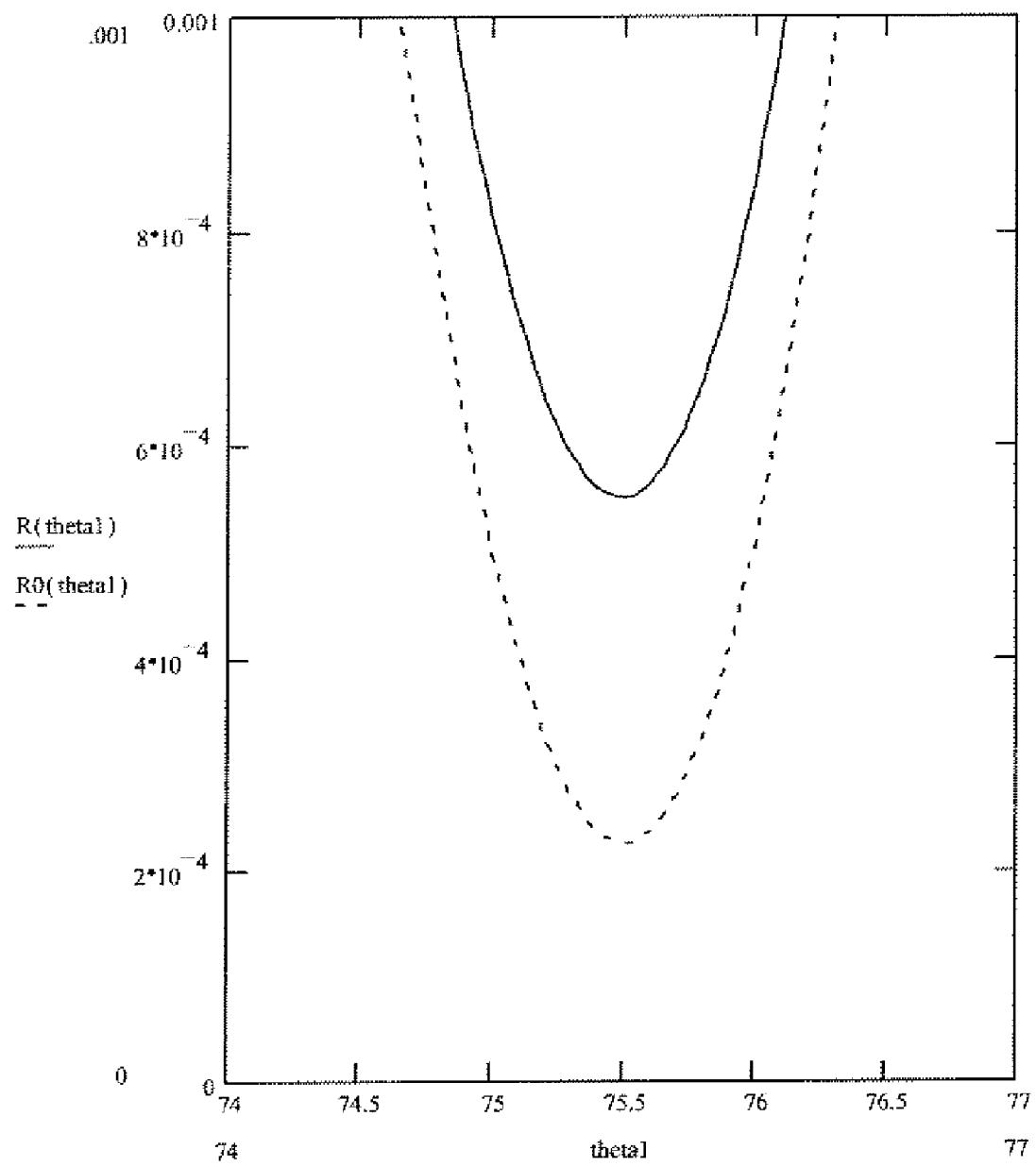
FIG. 5 is a graph showing reflectivity for air/oxide/silicon substrate with only 2 nm native oxide (dashed line) and with 2 nm oxide plus 1 nm additional material (solid line).

Once the optimal angle where near cancellation can occur is determined, both the value of the reflectivity minimum from Equation (1) and how it varies when layers are adsorbed on the oxide can be estimated. This is computed in FIG. 5 for the case where there is taken to be 2 nm of native oxide and the case where there is 2 nm of native oxide and an adsorbed layer 1 nm in thickness assumed to have the same refractive index as the oxide. This graph shows reflectivity versus incidence angle at the air/oxide interface. FIG. 5 shows that this variation of RI is very promising for sensing. First, the reflectivity more than doubles for 1 nm of adsorbed material—it is shown below that the relationship between minimum reflectivity and adsorbate is parabolic. Second, the incidence angle of the minimum does not vary appreciably with adsorbed layer thickness and the angular width over which the minimum is achieved is very large compared to what is computed for s-polarized RI (described above). What this means in practical terms is that relatively large angular divergence is well tolerated without degradation of sensitivity. Physically, the reason for this is that there are very small pathlength differences for the wave reflecting from the front and back of the "coating" layer 2 with angle in the p-polarized case because it is only a few nm thick as opposed to ~150 nm in the s-polarized case. A corollary, however, is that theoretically perfect Brewster straddle interferometry (p-polarized RI) is less sensitive to thickness changes than optimized s-polarized RI. In practice, however, the practical sensitivity limits between the two approaches are not that different because of the ability to achieve uniform and reproducible oxide thickness, and coherence problems can be overcome with collimation and monochromaticity.

Figure 6:
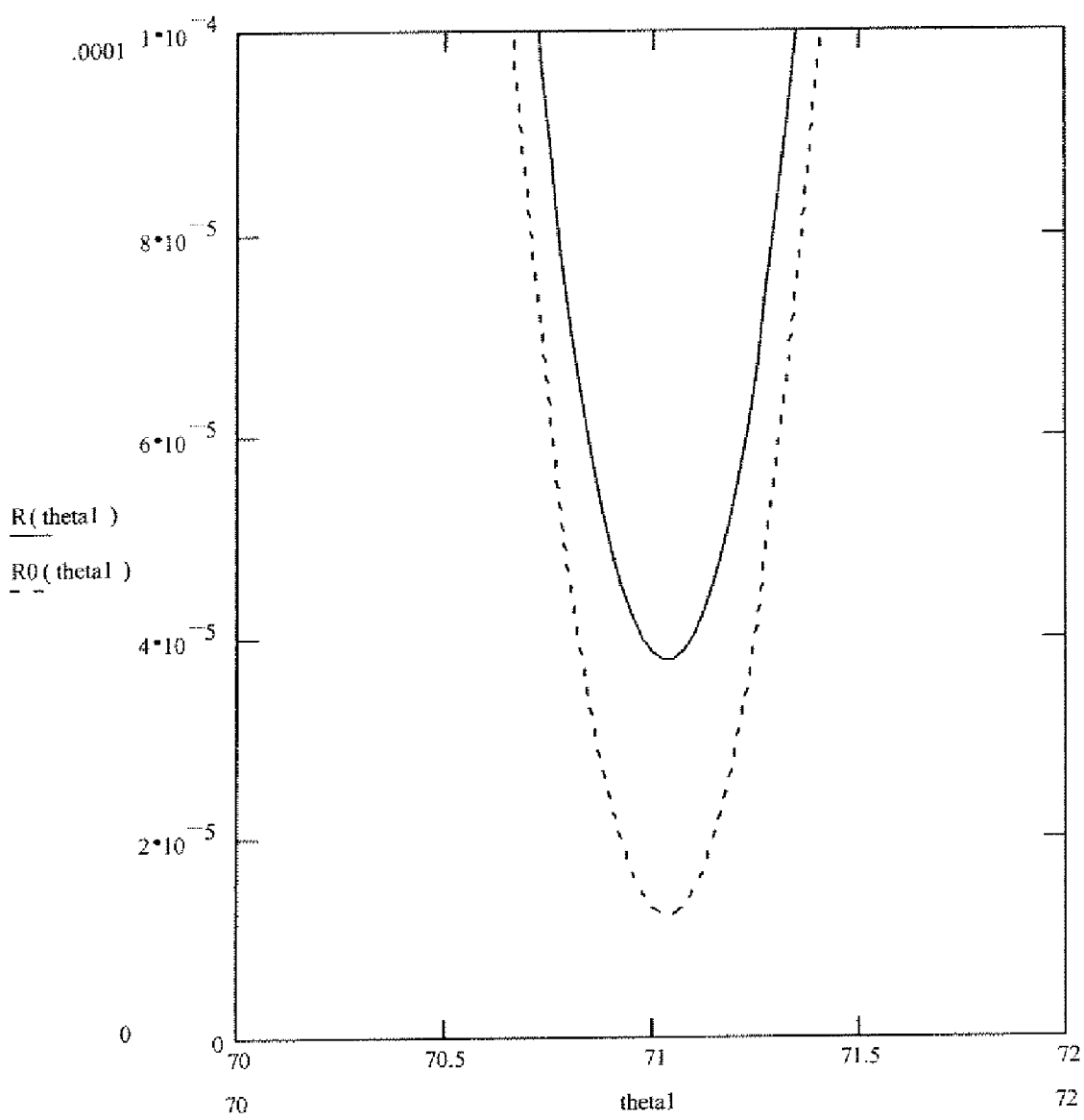
FIG. 6 is a graph showing reflectivity for air/oxide/silicon substrate with only 2 nm native oxide (dashed line) and with 2 nm oxide plus 1 nm additional material (solid line) where the incident light is in water. Theta refers to the angle in water.
Figure 13:
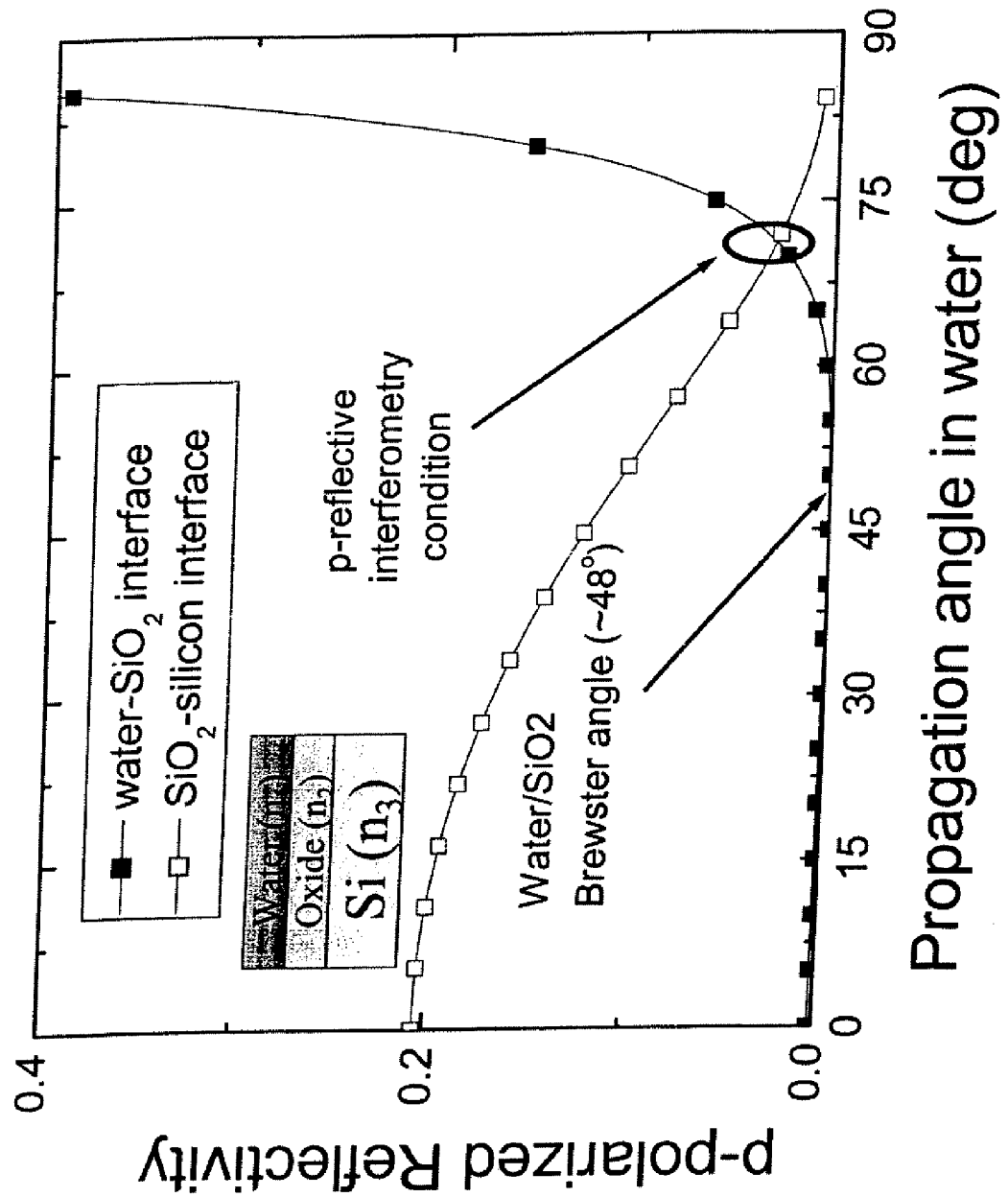
FIG. 13 is a graph illustrating the crossover in reflection from the two interfaces that makes p-polarized RI work. The reflection from the water/$SiO_2$ interface is above the Brewster angle (~48° for that interface) so it experiences a sign flip relative to the reflection at the $SiO_2$/silicon interface, which is below the Brewster angle. Thus, the reflections from the two interfaces interfere destructively at the crossover point (incident agent of about 71° in water or about 75.5° in air).

In the case of working under water, the physics is very similar and the angle for a reflectivity minimum is approximately 71° in water (see FIG. 13). Prism coupling can be used to achieve this angle just as in the s-polarized case although it is a much less steep angle (see FIG. 3). The reflectivity minimum in the water case is computed in FIG. 6 and the sensitivity for 1 nm adsorbed on a 2 nm native oxide is also shown to be a factor of 2. This graph shows reflectivity versus incidence angle at the water/oxide interface. It should be noted that the absolute magnitude of the reflection minimum in the water case is smaller than for the air case. Physically, this is because there is less reflection at the water/$SiO_2$ interface than at the air/$SiO_2$ interface. The same fraction of the reflectivity is cancelled by the interference since the oxide layer is the same thickness. Therefore, the same relative change in reflectivity (approximately a factor of 2) is made when a 1 nm layer of adsorbates with the same refractive index as the oxides is placed on the oxide.

Using approximate analytical theory, an analytic approximation to Equation (1) can be made if it is assumed that the adsorbates have the same refractive index as the oxide. It is instructive to do so and it turns out to give results very close to the full numerical solution. Hence, it is possible to quantify the amount of adsorbate by comparison with the reflectivity of the native oxide. In other words, a nearly quantitative topological map of the substrate based on its reflectivity using the simple analytical theory can be extracted. When $r_{12} \approx -r_{23}=r_0$, Equation (1) can be approximated as:

$$R=|r_0(1-\exp(-2i\beta))/(1+r_0^2\exp(-2i\beta))|^2 \qquad \text{Eq. (2)}$$

The value of $r_0^2$ is also much less than unity so the denominator can be taken to be approximately unity so that $R \approx r_0^2(1-\exp(-2i\beta))^2$. The value $\beta$ is much less than unity (since $d/\lambda$ is small, unlike the s-polarized case); thus, $\exp(-2i\beta) \approx 1-2i\beta$. The minimum reflectivity is then approximately R evaluated at the angle where $r_{12} \approx r_{23}$ and that simply reduces to:

$$R_{min}(d) \approx 4r_0^2\beta^2=[16\pi^2r_0^2n_2^2\cos^2\theta_2/\lambda^2]d^2 \qquad \text{Eq. (3)}$$

These are in good agreement with the calculation from Equation (1) so that these formulae can be used to translate reflectivity values into topology when the angular divergence of the laser is negligible.

The most important consequence of Equation (3) is that the value of the reflectivity minimum is expected to be parabolic with layer 2 thickness. To the extent that the refractive index of the adsorbates matches that of the oxide, one can write:

$$R_{min}(d_{tot})/R_{min}(d_{oxide})=(d_{tot}/d_{oxide})^2 \qquad \text{Eq. (4)}$$

and then see that a 1 nm adsorbate layer should produce $R_{min}=(3/2)^2 R_{oxide} \approx 2 R_{oxide}$ as computed above. The ability to measure 10% changes in reflectivity would give 1 Angstrom resolution. The reflectivity with respect to the oxide has been tested for several adsorbates and behaves according to the above expectation to within a factor of 2 in practice; thus, detection of ~1-2 Angstrom features is possible with Brewster straddle interferometry. This value is degraded for angular divergences that are large and it is therefore useful to have a full numerical theory to determine what "large" means.

Figure 7:
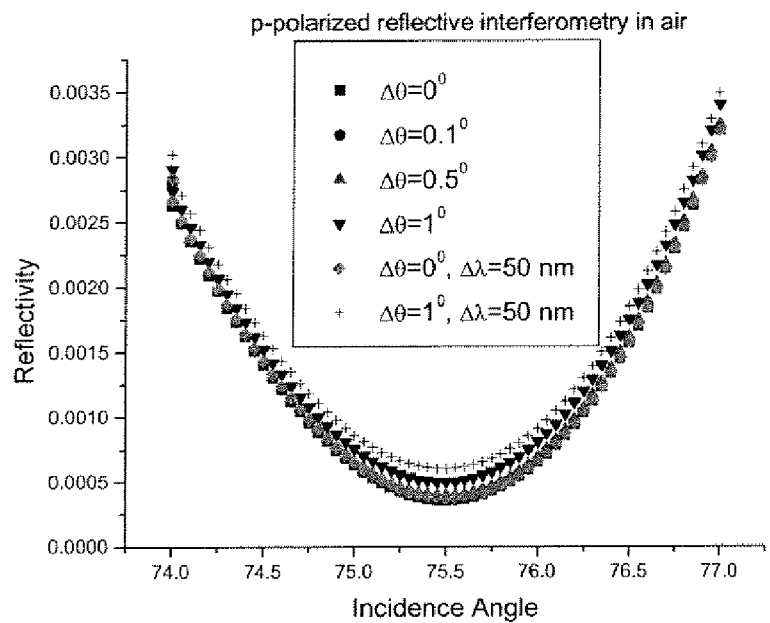
FIG. 7 is a graph showing reflectivity versus incidence angle in air with no adsorbates for various probe divergence and bandwidth.
Figure 8:
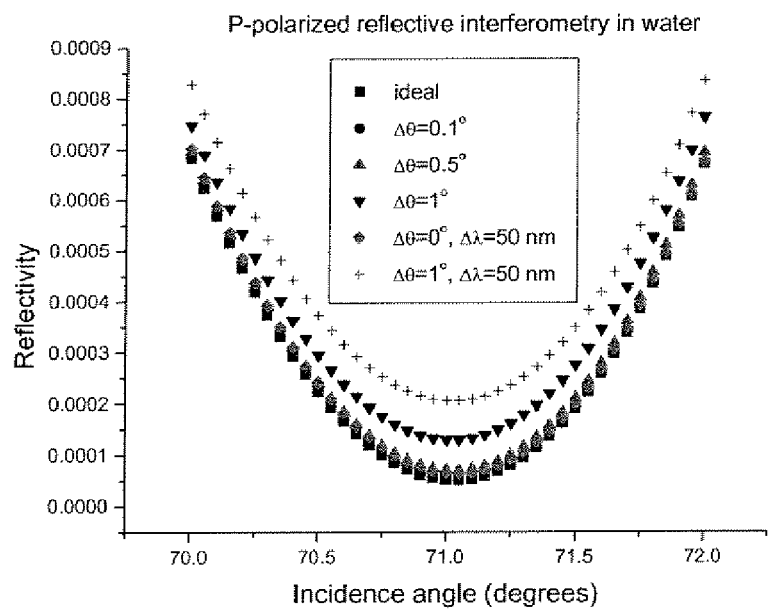
FIG. 8 is a graph showing reflectivity versus incidence angle in water with no adsorbates.
Figure 9:
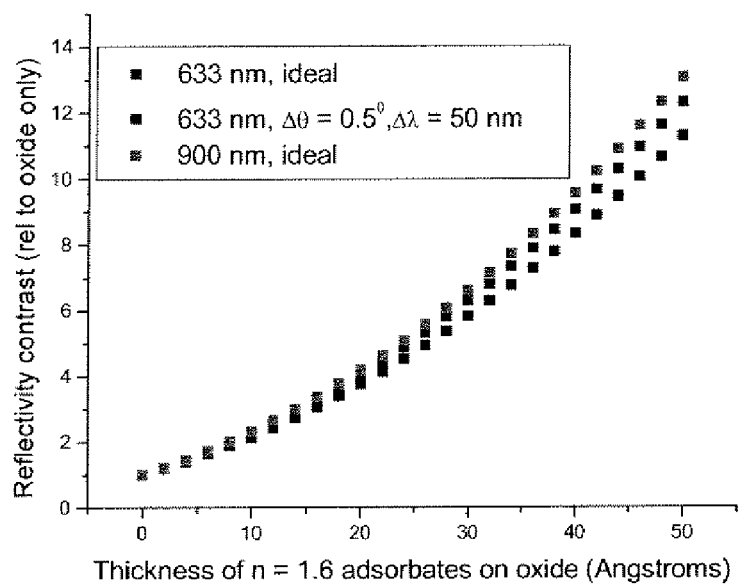
FIG. 9 is a graph showing reflectivity versus adsorbate thickness normalized to reflectivity with no adsorbate in air.
Figure 10:
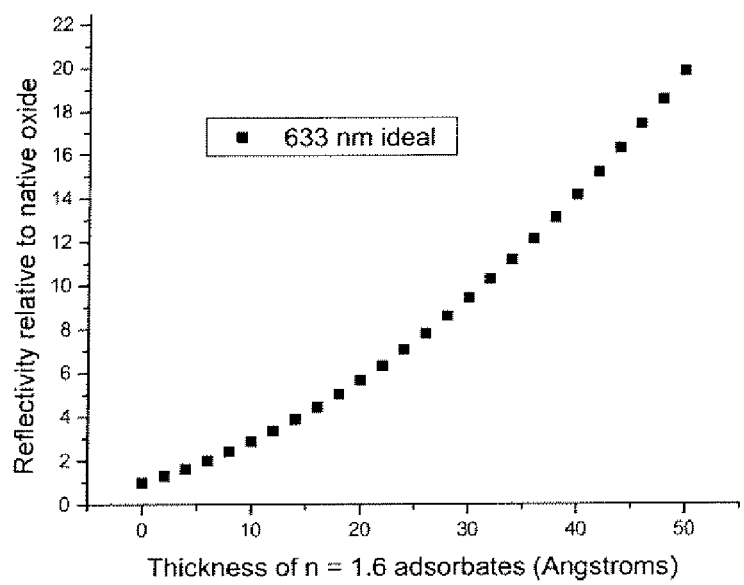
FIG. 10 is a graph showing reflectivity versus adsorbate thickness normalized to reflectivity with no adsorbate in water.

A full numerical theory to verify the above approximate computations was carried out using a transfer matrix formalism. In that theory, dispersion of the refractive index and differences in refractive index between oxide and the probe and target adsorbates can be accounted. Moreover, it is straightforward to model how the reflectivity minimum degrades with finite probe source divergence and bandwidth. FIGS. 7 and 8 depict the results of that modeling in air and water, respectively. Allowing for 0.5 degree angular divergence (~10 mrad) and 50 nm bandwidth around 633 nm results in little degradation of the sensitivity of the apparatus. Reflectivity versus thickness of adsorbed species can also be modeled and done relative to the oxide as well. Those data are shown in FIGS. 9 and 10 for air and water, respectively. These show parabolic relative reflectivity changes with thickness in good agreement with the analytical model above, and illustrate that the reflectance relative to that without adsorbates can be used to estimate adsorbate thickness. In addition, those values are nearly unchanged even when 0.5 degree angular divergence and 50 nm source bandwidth are introduced. Thus, it is practical to be quantitative even with only single color measurements as long as a reference spot with bare oxide can be provided. As with s-polarized RI, the sensitivity is better as the wavelength approaches red (e.g. 900 nm).

The scheme outlined according to the present invention is distinct from Brewster angle microscopy. A common approach to imaging submonolayer patterns of adsorbates at an interface is Brewster angle microscopy ("BAM"). The idea in BAM is that there is no reflection at the interface between materials 1 and 2 for p-polarized light when the incidence angle is Brewster's angle ($=\tan^{-1}(n_2/n_1)$). Adding adsorbates at the interface with $n \neq n_1$ or $n_2$ will turn on some reflectivity and enable imaging. This method is used to look at LB monolayers on the air-water interface, for example. In principle, this method could be used for biomolecular sensing at the glass-water interface where the substrate was a glass slide but there would be problems if, for example, the adsorbate index matched that of the glass.

The p-polarized RI method according to the present invention relies on interference between reflections from two separate interfaces, each of which has substantial reflection in that the probe light is not incident at the Brewster angle for either of the interfaces involved. Unlike BAM, the method outlined here would be effective even if the probe and target adsorbates have a refractive index identical to the oxide (they could not, however, have an index identical to the water in the aqueous measurement case). Brewster angle microscopy is, in principle, precisely a null method whereas the present method is not rigorously null. According to the present method, there is reflection from the $Si/SiO_2$ wafer even in the absence of any adsorbates. However, as shown above, that reflection can be used for quantitative calibration of the apparatus since the native oxide thickness is very uniform and reproducible.

In FIG. 2 the propagation angles for the light are denoted by $\theta$ and refractive indices by n. The coating 32 has a thickness h and the incident medium and the substrate 30 of the receptor 26 are assumed to be semi-infinite. It is assumed that there is a binder layer (not shown) between the coating 32 and the target analyte. In the analytical theory, it is also assumed that the binder layer has the same refractive index as the coating 32 and merely represents an increase in the thickness h of the coating 32.

Referring to FIGS. 1 and 2, the light source 22 is positioned to direct the light at the coating 32 on the substrate 30 at an angle of incidence which results in the desired Brewster angle straddle interference (which achieves near perfect interference). Under these conditions there is no reflectivity, and small changes in the absorption of a target or targets in the receptor 26 will cause large changes in reflectivity that can be easily measured. (Alternatively, any material or debris that is present on, e.g., the silicon dioxide coating can be detected.) By way of example only, an angle of incidence $\theta_4$ in air that is close to 75.5 degrees and an angle of incidence in an aqueous medium that is close to 71 degrees will achieve this condition. The use of p-polarized light, and the Brewster angle straddle interferometry provides a wider tolerance around the ideal angle of incidence than that which can be employed in s-polarization RI. Probe beam divergence of several degrees can still achieve results, with best results being obtained within about ±1 degree from the above-noted angles.

Figure 3:
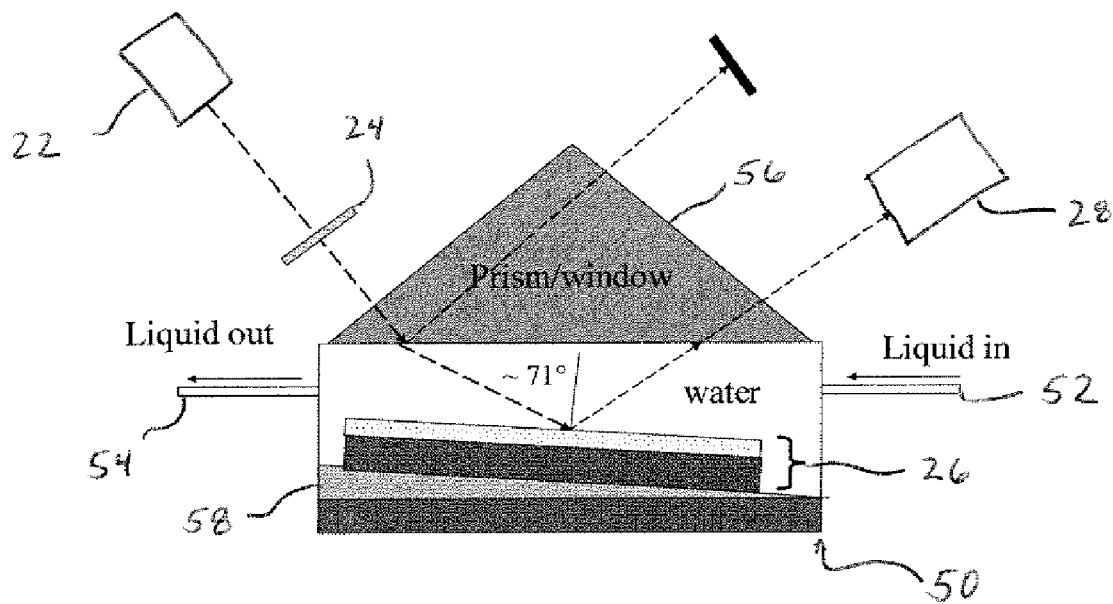
FIG. 3 is a side, cross sectional block diagram of a receptor for the biomolecular sensing system in accordance with another embodiment of the present invention. Specifically, the receptor is present in a flow cell that is designed for performing sensing operations in an aqueous environment. A wedge is provided beneath the receptor to afford the appropriate incident angle at the water/oxide interface while also allowing for spatial separation between reflections from the flow cell window and reflections from the substrate/oxide and water/oxide interfaces.

The aqueous embodiment is illustrated in FIG. 3. The flow cell 50 includes an inlet 52 and an outlet 54 through which aqueous medium is passed. The receptor 26 is positioned in the flow cell between the inlet and outlet, thereby allowing an target analyte in the aqueous medium to contact and bind an adsorbate bound to the coating on the receptor surface. To achieve the optimal 71 degree angle of incidence, coupling from the air with a prism 56 is used. Reflected light is also outcoupled through the prism. A wedge 58, formed of PDMS (polydimethylsiloxane) is provided beneath the substrate so that reflection from the substrate surface can be spatially discriminated from any reflections from the glass that confines the liquid.

Working in aqueous environment has many advantages, such as being able to use bodily fluids directly, eliminating the need for a rinsing step, and being able to monitor the binding kinetics in real time (i.e., through cumulative changes in reflectivity monitored continuously over a period of time, with greater reflectivity being detected as the concentration of adsorbed target molecules increases. The ability to monitor the kinetics can be useful in differentiating perfect oligonucleotide sequence matches from analytes with single base pair mismatches. Using fluorescent detection in an aqueous measurement is problematic since the entire liquid above the functionalized substrate 30 could contain fluorescent analytes. Since the present invention is only sensitive to changes at the interface, working under liquid will not pose analogous difficulties.

Sensitivity of the measurements can be improved to achieve near perfect interference comparable to that achieved using the s-polarized approach of Miller et al., described above. In other words, reflectivity of less than $10^{-5}$ or less than $10^{-6}$ can be achieved. According to one approach, the coating thickness can be adjusted from the very thin ($<<\lambda$) coating described above. According to another approach, background subtracted p-polarized RI can be utilized. Each of these approaches is described in greater detail below.

Sensitivity can be improved by adjusting coating thickness according to the formula $$\text{thickness}=m\lambda/(2n \cdot \cos \theta) \qquad \text{Eq (5)}$$

where m is an integer greater than zero (e.g., 1, 2, 3, etc.), n is the refractive index of the coating, $\lambda$ is the wavelength of the incident light, and θ is the angle of propagation from the normal in the coating. While coating thicknesses according to Equation 5 (and >>2 nm) should achieve comparable near perfect interference as described above, the required receptors would likewise suffer from the same disadvantages described above.

Figure 11:
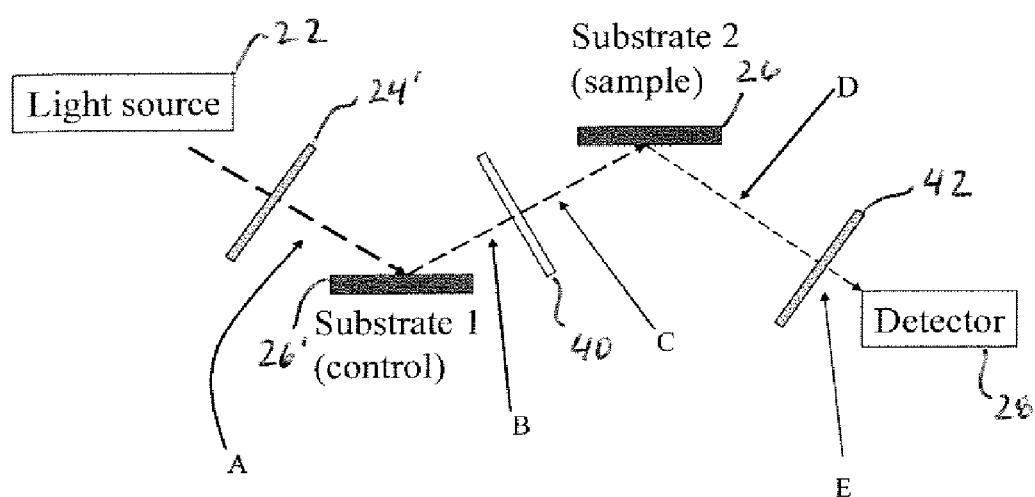
FIG. 11 illustrates a system according to one embodiment that employs phase mismatch correction in Brewster straddle interferometry.

Sensitivity can also be improved by using background subtracted p-polarized RI. The system illustrated in FIG. 1 would be modified to form a system as illustrated in FIG. 11. Light source 22 will emit light through an orthogonal (about 45°) polarizer 24' to a control receptor 26' that is identical to receptor 26 at least with regard to the substrate and coating (but may not be identical in regard to the adsorbate applied to the coating). In this case, polarizer 24' is set to allow approximately equal amounts of s-polarized and p-polarized light before reflection from the control receptor 26' (at A). Consequently, light with equal s- and p-polarization components reflect from the control surface at the angle appropriate to Brewster straddle interferometry (e.g., 71 degrees in water, 75.5 degrees in air for Si/SiO$_2$), whereby the p-component is nearly eliminated in the reflection (at B). The s-component has more back interface reflection and therefore lags the p-component (at B). A half wave plate 40 is positioned between the control receptor 26' and the receptor 26, allowing the s- and p-polarized light to switch with respect to receptor 26. Thus, the s-light from the control receptor 26' becomes p-polarized for the receptor 26 and the p-light from the control receptor 26' becomes the s-light (at C). The p-polarized light that contacts the receptor 26 is mostly cancelled (i.e., in the absence of analyte binding), whereas the s-polarized light that contacts receptor 26 lags the p-light by the same amount as it had led from the first substrate. Under these conditions, the light reflected from the sample receptor 26 will have just the opposite linear polarization that it began with (at D) so that it will be completely cancelled by an orthogonal (about 45°) polarizer 42 at the output (at E). If, however, the p-reflection is increased in magnitude on the sample receptor 26 (because the film thickness is increased by target analyte binding), then the magnitudes of p and s components will no longer match and the polarizer 42 will not extinguish the light perfectly. This should improve the sensitivity of the method by at least an order of magnitude.

As described above, the control and receptor substrates may or may not be identical with regard to functionalization of the coating surface. According to one embodiment, the two receptors are identical but the control receptor is not exposed to the analyte. According to another embodiment, the control receptor has a non-functionalized surface, in which case it can be exposed to the analyte without consequence. According to a further embodiment, the control receptor has a modified surface that is similar to the functionalized surface of the sample receptor. In this case, the adsorbate on the control receptor is structurally similar to the adsorbate of the sample receptor (i.e., similar thickness and refractive index), but the adsorbate of the control receptor is incapable of binding to the analyte of interest, in which case it can be exposed to the analyte without consequence. It is also worth noting that polarizations other than 45 degrees might work a little better empirically if the substrates are not identical. For example, if the control substrate were oxide only while the working substrate contained a layer for probe attachment chemistry that made it effectively thicker, subtraction would be imperfect when equal amounts of s- and p-light were used. Some of that imperfect subtraction could be improved by choosing to use slightly more s-light (i.e., incident polarizer not exactly 45 degrees) in order to approximately null the additional p-light that would be reflected from the thicker coating. An angle other than 45 degrees and, in general, also different than that for the incident polarizer would be optimal for the analyzing polarizer in this case to achieve best subtraction.

Although orthogonal polarizers are described in conjunction with the embodiment shown in FIG. 11, it should be appreciated by those of ordinary skill in the art that circular polarizers would also work in a similar manner since circular light also contains equal amounts of s and p.

The structures in FIGS. 1-3 and 11 are only several examples of using the Brewster angle straddle interference, and the implementation using silicon with its thermal oxide is just one implementation found to be practical. It is worth noting, however, that silicon is easy to obtain and process (no separate coating step, only coupling of adsorbates or probes) and there is no reflection from the back side of the substrate 30. For this reason, silicon and its native oxide coating are preferred.

Incorporating the modeling and the different possible arrangements discussed above, the operation of the sensing system 20 will be discussed with reference to FIGS. 1 and 2. Initially, a measurement may be taken before a sample which may contain one or more targets is introduced to the receptor 26. The light source 22 generates collimated light which is transmitted towards a coating 32 on the substrate 30 in the receptor 26. The wavelength band is relatively non-critical and is selected based on the requirements to achieve Brewster angle straddle interference (i.e., based on the relative refractive indices of the medium, coating, and substrate). The angle of incidence of the light with respect to the surface 36 of the receptor 26 is selected optimally to result in near perfect interference as defined above. The light is directed through a polarizer 24 which passes substantially only p-polarized light. The polarized light strikes and is reflected off of the coating 32. Nonidealities, such as surface roughness, finite beam divergence, and finite bandwidth reduce the sensitivity of the sensing system 20 much less than for s-reflective RI. The detector 28 measures the initial reflected light and produces an output of the initial measurement. The detector 28 may take an image of an array of spots with various probe molecules on the surface 36.

Next, a sample with one or more targets (of the type described above) is introduced, near the receptor 26, thereby allowing the targets to attach to and/or be the coating 32 in the receptor 26. Another measurement is taken after the sample is introduced to the receptor 26. The light source again transmits p-polarized light towards the coating 32 on the substrate 30 in the receptor 26, and is reflected off of the coating 32 absorbed targets. Adsorbing the targets at the surface of the coating 32 disturbs the interference condition and leads to increased reflectivity. The detector 28 measures the reflected light which can be used to determine the amount of adsorbed species. A variety of different processing techniques can be used on the initial and exposed measurement as required by the particular application, such as monitoring the growth of a particular target or identifying the presence of a particular target. The monitoring can also be carried out continuously to monitor reaction kinetics real time.

In another possible implementation, the mere presence of molecular debris on the surface of a silicon wafer can be detected. Basically, near perfect interference is achieved only in the absence of any material on the oxide surface, and the presence of any debris can be detected relative to a clean oxide coating. This use of the present invention is highly desirable in, e.g., quality control analysis of semiconductor wafer fabrication processes.

The simple scheme for the sensor discussed above can also be used for larger scale arraying of biological materials. The only difference is that the detector 28, such as a CCD camera, images a substantial portion of the coating 32 of the receptor 26. The advantages of arraying are numerous. One can do many simultaneous experiments, look for many different analytes, or do pattern analysis where binding is not perfectly specific. Another advantage is that untreated areas can be easily used as a reference to more accurately measure the additional thickness due to analyte binding. Often, adsorption occurs non-uniformly (perhaps due to solvent evaporation during dosing causing droplets to shrink) so that the actual deposition of binder and analyte can be quite inhomogeneous. This can be detected more easily with an imaging method and one could apply numerical procedures similar to those used for fluorescent assays to properly account for the non-uniformity.

EXAMPLES

The following examples are provided to illustrate embodiments of the present invention but are by no means intended to limit its scope.

Example 1

P-polarized Reflective Interferometry Using Brewster Angle Flip

P-polarized RI has been reduced to practice both under air and under aqueous media by imaging reflection from adsorbate layers that have been independently measured with spectroscopic ellipsometry. P-polarized RI also has potential uses for sensing. The apparatus is essentially identical to that used in standard reflective interferometry except that the incident probe light is p-polarized, the incidence angle is as computed above and the substrate under test is a silicon wafer with only a ~2.5 nm native oxide. For the data shown below, the probe source was a spatially filtered, collimated and apertured HeNe laser beam.

Figure 12A:
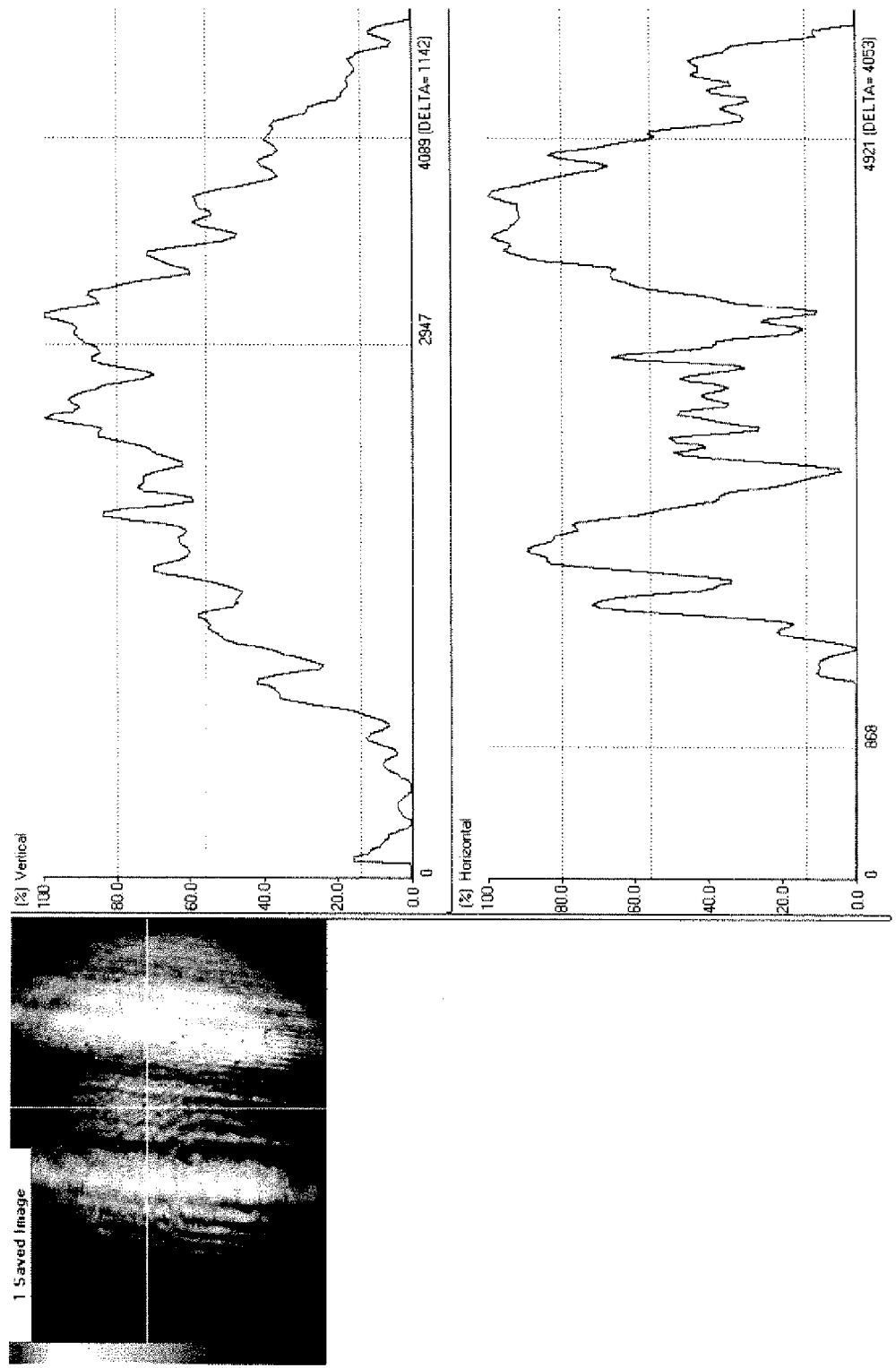
FIGS. 12A-D show a false color photograph of the reflection from a substrate using the intensity color code bar on the left side of the figure.
Figure 12B:
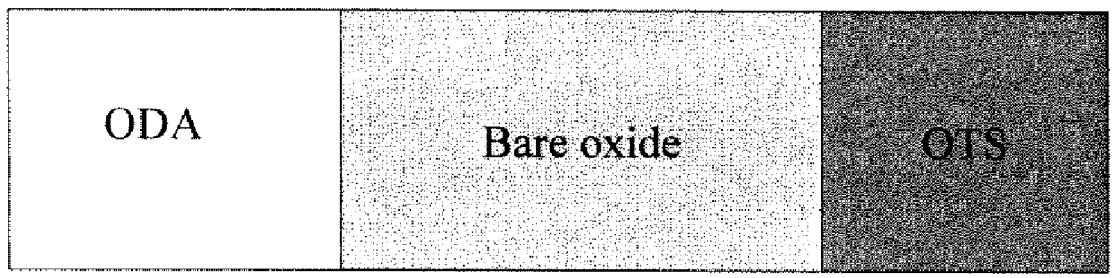

FIG. 12A shows a false color photograph of the reflection from a substrate using the intensity color code bar on the left. The composition of the substrate is sketched in FIG. 12B. The left of the FIG. 12B corresponds to PDMS stamped octadecylamine (ODA), the middle is bare native oxide and the right is octadecyl tricholorosilane (OTS) treated to form a covalent SAM. Ellipsometry verifies that the bare oxide is around 28 Angstroms, the oxide plus ODA is around 38 Angstroms and the oxide plus OTS is around 50 Angstroms. The right panels of FIG. 12A are intensity versus position along the crosshairs. Note that the structure is due to interference and is not noise. The s-polarized reflection is fairly smooth.

The intensity data from FIG. 12A cannot be converted to thickness and directly compared with the theory because one must also account for the fact that the beam intensity is not spatially uniform. In practice, this would be done by using s-polarized light to measure the beam intensity profile or by using a beam tailored to have very flat intensity profile. In the above case, that measurement was not made. The approximate profile is given by the vertical slice (upper panel) through the oxide.

Figure 12C:
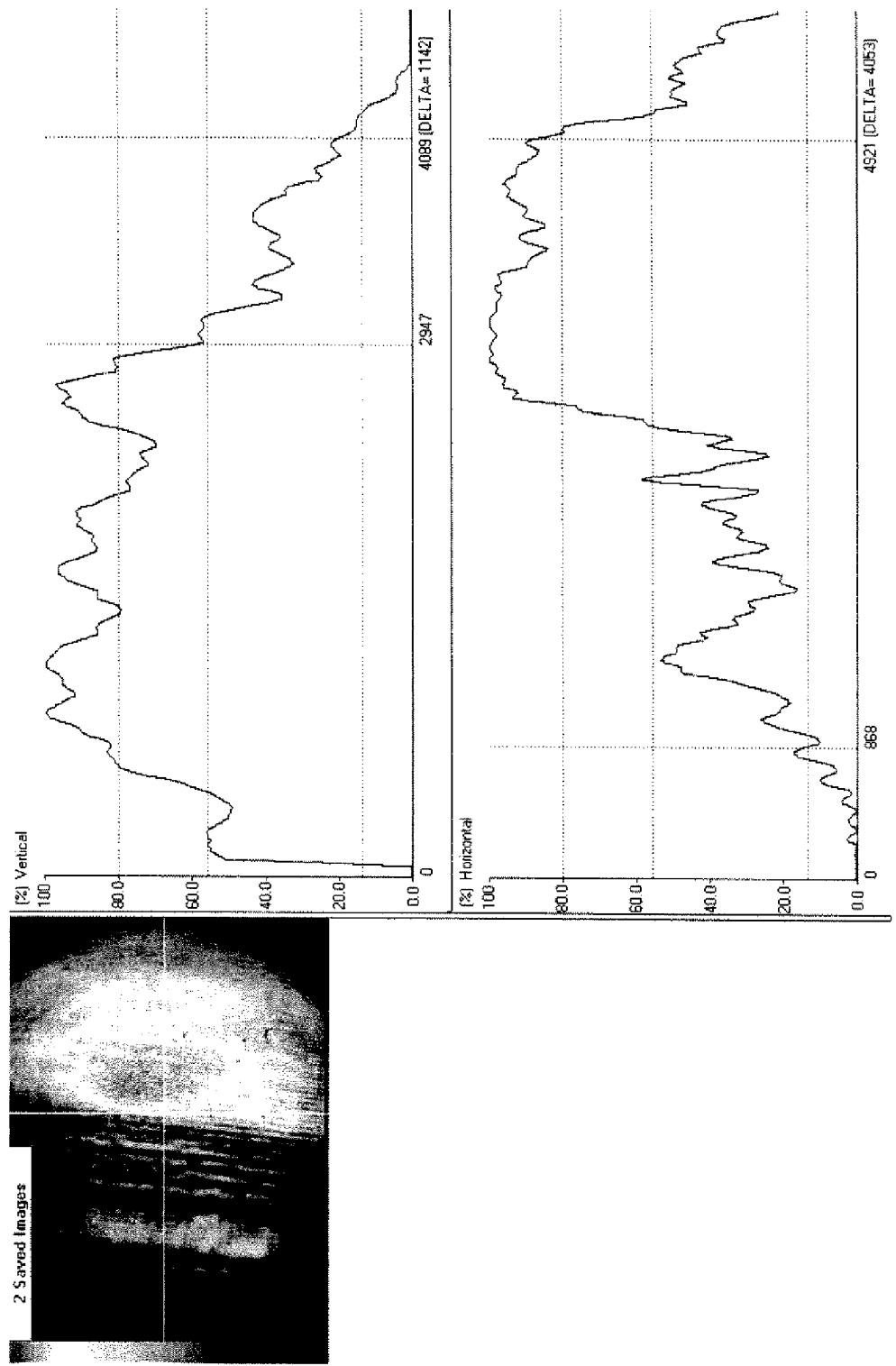

To determine whether the result agrees with theory, the trick of moving the substrate so that the center of the probe beam where the intensity is fairly uniform resides at the interface between the bare oxide and OTS was employed. These data are shown in FIG. 12C and a comparison of the reflectivity on either side of the interface shows that the ~2 nm OTS layer gives reflectivity around 3-4 times that of the oxide. This is in rough agreement with the estimate of $(50/28)^2$ predicted by theory.

Figure 12D:
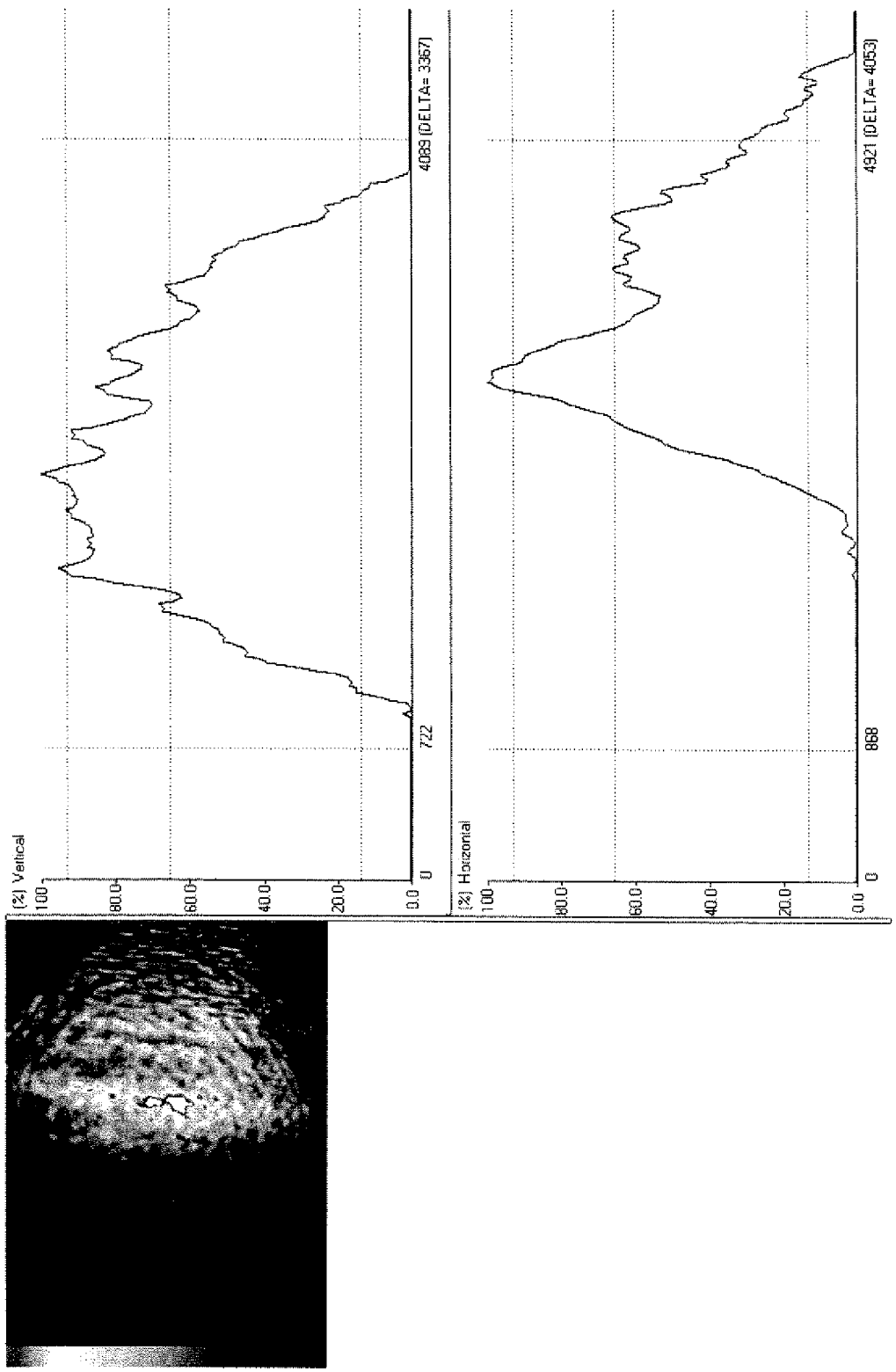

Finally, it is possible to show that p-polarized RI can also be applied under water. The angle of incidence is much less steep than for s-polarized RI which is likely to be helpful in properly implementing the method. Prism coupling to achieve that angle is, however, still necessary. FIG. 12D illustrates the reflectivity from the same substrate as in FIG. 12C with the beam positioned as in FIG. 12C, but now under water. Prism coupling is used to achieve the appropriate angle. The substrate is mounted on a small wedge so that reflection from the substrate surface can be spatially discriminated from reflections from the glass that confines the liquid. The contrast appears to be even larger than predicted by theory.

Example 2

Binding Chemistry

Any selective binding chemistry that can be implemented on the receptor can produce an adequate sensor. In one example, the receptor is rinsed and dried before imaging the surface topology of the coating. This is important to do to reduce any non-selective binding.

In this example, the surface is functionalized by silanization with 3-aminopropyltrimethoxysilane ("APTES") followed by glutaraldehyde ("GA") This in turn binds to streptavidin. This initial surface is relatively easy and rapid to prepare. The streptavidin surface is reasonably immune to non-specific binding and strongly binds biotinylated compounds. Since many biotinylated oligomers and antibodies are commercially available, this chemistry is easily implemented to make the receptor.

Example 3

Arrayed Detection Of Target RNA Using 2-O-Methyl RNA Probes

Two 2-O-methyl RNA probes were assembled for detection of a 47-mer fragment of mutant Ha-ras mRNA, an important therapeutic target for antisense oligonucleotide treatments of cancer (Lima et al., *Biochemistry* 31:12055-12061 (1992), which is hereby incorporated by reference in its entirety). The probes, designated M3291 (strongly binding) and M3292 (very weak binding), have solution affinities as reported previously by Lima et al. (cited above). M3291 is complementary to the hairpin loop while M3291 is complementary to the stem and a small part of the hairpin loop. The latter is found to bind $10^7$ times more slowly in solution than the former. The chip had immobilized 2O'-methyl RNA oligos and was organized as shown in FIG. 16A (lower left).

This array was mounted in an aqueous system of the type illustrated in FIG. 3, and used to detect binding of R47 RNA. Detection of changes in the reflectivity was carried using a CCD camera and a lamp filtered through a ~25 nm bandpass filter at about 650 nm. The images presented in FIG. 16B of the reflected beam before (left image) and after (right image) application of R47 target. FIG. 16C illustrates an intensity cross-section of the image showing clearly that binding to the M3291 occurs while binding to the M3292 does not. These results are in agreement with the solution studies cited above.

These results are useful not only in detection of the presence of R47 RNA, for example, but can also be used to determine what R47 sequences are surface exposed on the three-dimension structure thereof (i.e., the probe sequences are known). Hence, knowing the probe sequence, the array data can be used infer (or confirm its predicted) three-dimensional structure. Data like those in FIG. 16B-C on thickness calibrated OTS thin films show that p-polarized RI reflection increases agree with those predicted by theory to within a factor of 2. Thus, the method is nearly quantitative.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. A sensor system for sensing at least one target in a medium, the system comprising:
    a receptor for the at least one target, the receptor comprising a silicon substrate and a translucent native oxide coating on the substrate, the coating having front and back surfaces and one or more adsorbates attached to the front surface of the coating, said one or more adsorbates being capable of recognizing the at least one target;
    a source of p-polarized light positioned to direct at least a portion of the p-polarized light from the source toward the coating on the receptor in a manner effective to result in a condition of near perfect interference where reflectivity is less than $10^{-3}$ in the absence of a target bound to the one or more adsorbates on the receptor, wherein the incident angle for one of the substrate/coating interface and the medium/coating interface is greater than its Brewster angle and the incident angle for the other interface is less than its Brewster angle; and
    a detector positioned to measure the light reflected from the front and back surfaces of the coating, the detector identifying presence of at least one target based on a change in the measured reflected light.

2. The system according to claim 1 wherein the incident angle for the substrate/coating interface is greater than its Brewster angle and the incident angle for the medium/coating interface is less than its Brewster angle.

3. The system according to claim 1 wherein the incident angle for of the medium/coating interface is greater than its Brewster angle and the incident angle for the substrate/coating interface is less than its Brewster angle.

4. The system according to claim 1 wherein the medium is an aqueous medium.

5. The system according to claim 4 further comprising at least one prism in a path of the at least a portion of the p-polarized light.

6. The system according to claim 1 wherein the medium is air.

7. The system according to claim 1 wherein the native oxide coating is between about 1 and about 3 nm.

8. The system according to claim 1 wherein the native oxide coating is about 2.5 nm.

9. The system according to claim 1 wherein the incident angle for the medium/coating interface is 71 degrees ±2 degrees in an aqueous medium.

10. The system according to claim 1 wherein the incident angle for the medium/coating interface is 75.5 degrees ±2 degrees in air.

11. The system according to claim 1 wherein the source of p-polarized light comprises:
    a non-polarized light source and
    a polarizer that induces p-polarization of at least a portion of light emitted by the non-polarized light source or reflected from the receptor.

12. The system according to claim 1 wherein the source of p-polarized light is a laser that emits substantially only p-polarized light.

13. The system according to claim 1 wherein the one or more adsorbates are selected from the group of non-polymeric small molecules, polypeptides or proteins, oligonucleotides, and combinations thereof.

14. The system according to claim 1 wherein the coating further comprises a coupling agent that links the one or more adsorbates to the coating.

15. The system according to claim 1 wherein the light source is selected from the group of a laser, a light-emitting diode, and lamp comprising a narrow bandpass filter.

16. The system according to claim 1 wherein the detector is an imaging array, photomultiplier, CCD, or photodiode that captures an image of at least a substantial portion of the surface of the receptor.

17. A method for sensing at least one target, the method comprising:
    providing a system according to claim 1;
    directing p-polarized light at the receptor in a manner effective to achieve, in the absence of at least one target, a condition of near perfect interference between light reflected from the medium/probe interface and light reflected from the substrate/coating interface; and
    measuring the light reflected from the interfaces of the receptor, wherein measurement of light reflected the interfaces indicates presence of the at least one target.

18. The method according to claim 17 further comprising:
    providing an output identifying the at least one target based on the measured reflected light.

19. The method according to claim 17 wherein the measuring the reflected light further comprises capturing an image of at least a substantial portion of the surface of the receptor.

20. The method according to claim 17 further comprising:
    repeating said measuring before and after exposure of the receptor to a sample comprising the at least one target; and
    comparing the measurement of reflected light from said measurements.

21. The method according to claim 20 further comprising:
    quantifying the amount of at least one target present on the receptor.

22. The method according to claim 21 further comprising:
    quantifying the concentration of the at least one target present in the sample.

23. The method according to claim 17 wherein the target is selected from the group of proteins, glycoproteins, peptidoglycans, carbohydrates, lipoproteins, lipoteichoic acids, lipid A, phosphates, nucleic acids, whole cells, virus particles, organic toxins, organic warfare agents.

24. The method according to claim 17 wherein said measuring occurs continuously over a predetermined period of time.

25. A method of inspecting a semiconductor wafer comprising:
    providing a semiconductor wafer comprising a substrate and a coating thereon;
    directing p-polarized light toward the semiconductor wafer in a manner effective to result in a condition of near perfect interference where reflectivity is less than $10^{-3}$ in the absence of any debris on the surface of the semiconductor wafer, wherein the incident angle for one of the substrate/coating interface and the medium/coating interface is greater than its Brewster angle and the incident angle for the other interface is less than its Brewster angle; and measuring the light reflected from the interfaces of the semiconductor wafer at one or more locations over the surface of the semiconductor wafer, wherein the measuring of a change in the reflected light indicates the presence of debris on the surface of the semiconductor wafer.

26. The method according to claim 25 wherein the semiconductor wafer is an unassembled semiconductor wafer.

27. The method according to claim 25 wherein the semiconductor wafer comprises a silicon substrate and a silicon dioxide coating.

* * * * *